United States Patent [19]
Levy

[11] Patent Number: 5,817,793
[45] Date of Patent: Oct. 6, 1998

[54] MULTIPLE ANTIBIOTIC RESISTANCE OPERON ASSAYS

[75] Inventor: Stuart B. Levy, Boston, Mass.

[73] Assignee: Trustees of Tufts College, Medford, Mass.

[21] Appl. No.: 225,480

[22] Filed: Apr. 8, 1994

Related U.S. Application Data

[63] Continuation-in-part of Ser. No. 938,085, Aug. 28, 1992, abandoned.
[51] Int. Cl.$^6$ .................................................. C07H 21/04
[52] U.S. Cl. ...................................... 536/24.1; 536/24.32
[58] Field of Search ................................ 536/24.1, 24.5, 536/23.7, 24.32; 514/44

[56] References Cited

FOREIGN PATENT DOCUMENTS

WO92/04458   3/1992   WIPO .

OTHER PUBLICATIONS

George, A. et al., Gene in the Major Cotransduction Gap of the Escherichia coli K–2 Linkage Map Required for the Expression of Chromosomal Resistance to Tetracycline and Other Antibiotics, J. of Bacteriology, vol. 155, No. 2, Aug. 1983, pp. 541–548.
George, A. et al., Amplifiable Resistance to Tetracycline, Chloramphenicol, and Other Antibiotics in Escherichia coli: Involvement of a Non–Plasmid–Determined Efflux of Tetracycline, J. of Bacteriology, vol. 155, No. 2, Aug. 1983, pp. 531–540.
Cohen, S. et al., marA Locus Causes Decreased Expression of OmpF Porin in Multiple–Antibiotic–Resistant (Mar) Mutants of Escherichia coli, J. of Bacteriology, vol. 170, No. 12, Dec. 1988, pp. 5416–5422.
Choen, S. et al., Cross–Resistance to Fluoroquinolones in Multiple–Antibiotic–Resistant (Mar) Escherichia coli Selected by Tetracycline of Chloramphenicol: Decreased Drug Accumulation Associated with Membrane Changes in Addition to OmpF Reduction, Antimicrobial Agents and Chemotherapy, vol. 33, No. 8, Aug. 1989, pp. 1318–1325.
Hachler, H. et al., Genetic Organization of marA, A Chromosomal Locus that Controls Multiple Antibiotic Resistance in Escherichia coli, 50th Annual Meeting Swiss Soc. Microbiol., Apr. 4–6, 1991, abstract.
Cohen, S. et al., Transcriptional Activation of the marA Locus of Escherichia coli by Growth in Salicylate, ASM Meeting, May 5–9, 1991, abstract.

Hachler, H. et al., marA, a Regulated Locus Which Controls Expression of Chromosomal Multiple Antibiotic Resistance in Escherichia coli, J. of Bacteriology, vol. 173, No. 17, Sep. 1991, pp. 5532–5538.
Yan, W. et al., Three Putative Proteins in the mar Operon Mediate Intrinsic Multidrug Resistance in Escherichia coli, ASM Meeting, May 1992, abstract.
Cohen, S. et al., Conservation of mar Sequences among Members of the Enterobacteriaceae, ASM Meeting, May 1992, abstract.
Miller, P. et al., Molecular Cloning and Characterization of a Gene Conferring High–Copy–Number–Dependent Multidrug Resistance in Escherichia coli, ASM Meeting, May 1992, abstract
Koh, C. et al., "Plasmid–mediated transferable multiple antibiotic resistance in a clinical isolate of the bacterium Providencia sp. in Penninsular Malaysia," p. 404, Chemical Abstracts, vol. 107, No. 17, Oct. 26, 1987.
Choi, E. et al., "The Cloning of MLS Antibiotics Inducible Resistance Gene", Jan. 15, 1990, p. 153, Chemical Abstracts, vol. 112 No. 3.
Gambino, L. et al., Overexpression of the MarA Positive Regulator Is Sufficient To Confer Multiple Antibiotic Resistance in Escherichia coli, J. of Bact., V175, n10, May 1993, 2888–2894.
Cohen, S. et al., Genetic and Functional Analysis of the Multiple Antibiotic Resistance (mar) Locus in Escherichia coli, J. of Bact., V175, n5, Mar. 1993, 1484–1492.
Ariza, R. et al., Repressor Mutations in the marRAB Operon That Activate Oxidation Stress Genes and Multiple Antibiotic Resistance in Escherichia coli, J. of Bacteriology, vol. 176, No. 17, Jan. 1994, pp. 143–148.
Cohen, S. et al., Salicylate Induction of Antibiotic Resistance in Escherichia coli: Activation of the mar Operon and a mar–Independent Pathway, J. of Bacteriology, vol. 175, No. 24, Dec. 1993, pp. 7856–7862.

Primary Examiner—Scott W. Houtteman
Attorney, Agent, or Firm—Wolf, Greenfield & Sacks, P.C.

[57] ABSTRACT

An isolated and cloned region of a bacterial chromosome containing a multiple antibiotic resistance operon is disclosed. A description of the structure and function of the operon is provided as are assorted recombinant DNA constructs involving the operon or fragments thereof. The diagnostic, therapeutic and experimental uses of these constructs are also disclosed. Methods of evaluating the antibiotic effectiveness of compositions are disclosed and methods of treatment employing effective compositions are provided.

27 Claims, 1 Drawing Sheet

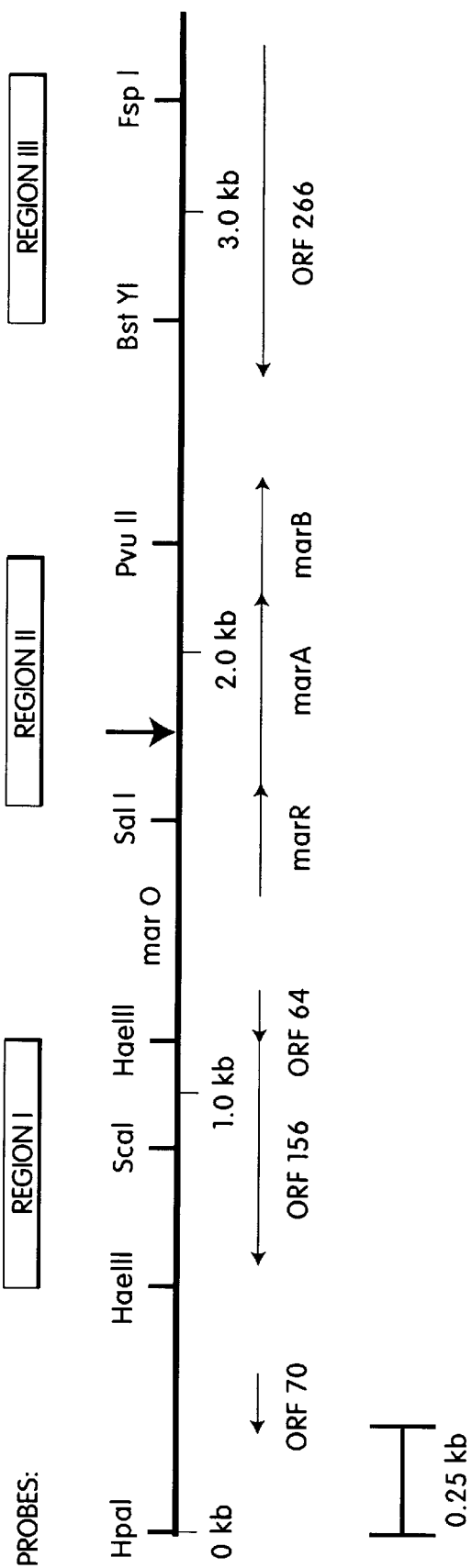

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 7876 base pairs
        ( B ) TYPE: nucleic acid
        ( C ) STRANDEDNESS: double
        ( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:
      ( A ) ORGANISM: Escherichia coli ( i x ) FEATURE:
      ( A ) NAME/KEY: CDS
      ( B ) LOCATION: complement (572..1042)
      ( D ) OTHER INFORMATION: /gene= "ORF156/157"
         / note= "Start codon indefinite. ORF 157 at complement 572..1042. ORF 156 at complement 572..1039. For ORF 157, first GTG encodes Met."

( i x ) FEATURE:
      ( A ) NAME/KEY: CDS
      ( B ) LOCATION: complement (1042..1233)
      ( D ) OTHER INFORMATION: /gene= "ORF 64"

( i x ) FEATURE:
      ( A ) NAME/KEY: CDS
      ( B ) LOCATION: 1445..1876
      ( D ) OTHER INFORMATION: /gene= "marR"
         / transl_except= (pos: 1445 .. 1447, aa: Met)

( i x ) FEATURE:
      ( A ) NAME/KEY: CDS
      ( B ) LOCATION: 1893..2279
      ( D ) OTHER INFORMATION: /gene= "marA"

( i x ) FEATURE:
      ( A ) NAME/KEY: CDS
      ( B ) LOCATION: 2314..2529
      ( D ) OTHER INFORMATION: /gene= "marB"

( i x ) FEATURE:
      ( A ) NAME/KEY: CDS
      ( B ) LOCATION: complement (2566..3363)
      ( D ) OTHER INFORMATION: /gene= "ORF 266"

( i x ) FEATURE:
      ( A ) NAME/KEY: promoter
      ( B ) LOCATION: 1234..1444
      ( D ) OTHER INFORMATION: /standard_name= "marO"

( x i ) SEQUENCE DESCRIPTION: SEQ ID NO:1:

```
GTTAACTGTG GTGGTTGTCA CCGCCCATTA CACGGCATAC AGCTATATCG AGCCTTTTGT      60
ACAAAACATT GCGGGATTCA GCGCCAACTT TGCCACGGCA TTACTGTTAT TACTCGGTGG     120
TGCGGGCATT ATTGGCAGCG TGATTTTCGG TAAACTGGGT AATCAGTATG CGTCTGCGTT     180
GGTGAGTACG GCGATTGCGC TGTTGCTGGT GTGCCTGGCA TTGCTGTTAC CTGCGGCGAA     240
CAGTGAAATA CACCTCGGGG TGCTGAGTAT TTTCTGGGGG ATCGCGATGA TGATCATCGG     300
GCTTGGTATG CAGGTTAAAG TGCTGGCGCT GGCACCAGAT GCTACCGACG TCGCGATGGC     360
GCTATTCTCC GGCATATTTA ATATTGGAAT CGGGGCGGGT GCGTTGGTAG GTAATCAGGT     420
GAGTTTGCAC TGGTCAATGT CGATGATTGG TTATGTGGGC GCGGTGCCTG CTTTTGCCGC     480
GTTAATTTGG TCAATCATTA TATTTCGCCG CTGGCCAGTG ACACTCGAAG AACAGACGCA     540
ATAGTTGAAA GGCCCATTCG GGCCTTTTTT AATGGTACGT TTTAATGATT CCAGGATGC      600
CGTTAATAAT AAACTGCACA CCCATACATA CCAGCAGGAA TCCCATCAGA CGGGAGATCG     660
CTTCAATGCC ACCCTTGCCC ACCAGCCGCA TAATTGCGCC GGAGCTGCGT AGGCTTCCCC     720
ACAAAATAAC CGCCACCAGG AAAAAGATCA GCGGCGGCGC AACCATCAGT ACCCAATCAG     780
CGAAGGTTGA ACTCTGACGC ACTGTGGACG CCGAGCTAAT AATCATCGCT ATGGTTCCCG     840
GACCGGCAGT ACTTGGCATT GCCAGCGGCA CAAAGGCAAT ATTGGCACTG GGTTCATCTT     900
CCAGCTCTTC CGACTTGCTT TTCGCCTCCG GTGAATCAAT CGCTTTCTGT TGCGGAAAGA     960
```

```
GCATCCGAAA ACCGATAAAC GCGACGATTA AGCCGCCTGC AATTCGCAGA CCGGGAATCG    1020

AAATGCCAAA TGTATCCATC ACCAGTTGCC CGCGTAATAC GCCACCATCA TGATGGCAAA    1080

TACGTACACC GAGGCCATCA ACGACTGACG ATTACGTTCG GCACTGTTCA TGTTGCCTGC    1140

CAGGCCAAGA AATAACGCGA CAGTTGTTAA TGGGTTAGCT AACGGCAGCA ACACCACCAG    1200

CCCCAGGCCA ATTGCTTTAA ACAAATCTAA CATTGGTGGT TGTTATCCTG TGTATCTGGG    1260

TTATCAGCGA AAAGTATAAG GGGTAAACAA GGATAAAGTG TCACTCTTTA GCTAGCCTTG    1320

CATCGCATTG AACAAAACTT GAACCGATTT AGCAAAACGT GGCATCGGTC AATTCATTCA    1380

TTTGACTTAT ACTTGCCTGG GCAATATTAT CCCCTGCAAC TAATTACTTG CCAGGGCAAC    1440
```

| | | | | | | | | | | | | | | | | |
|---|---|---|---|---|---|---|---|---|---|---|---|---|---|---|---|---|
|TAAT|GTG|AAA|AGT|ACC|AGC|GAT|CTG|TTC|AAT|GAA|ATT|ATT|CCA|TTG|GGT|1489|
| |Met|Lys|Ser|Thr|Ser|Asp|Leu|Phe|Asn|Glu|Ile|Ile|Pro|Leu|Gly| |
| |1| | | |5| | | | |10| | | | |15| |

| | | | | | | | | | | | | | | | | |
|---|---|---|---|---|---|---|---|---|---|---|---|---|---|---|---|---|
|CGC|TTA|ATC|CAT|ATG|GTT|AAT|CAG|AAG|AAA|GAT|CGC|CTG|CTT|AAC|GAG|1537|
|Arg|Leu|Ile|His|Met|Val|Asn|Gln|Lys|Lys|Asp|Arg|Leu|Leu|Asn|Glu| |
| | | | |20| | | | |25| | | | |30| | |

| | | | | | | | | | | | | | | | | |
|---|---|---|---|---|---|---|---|---|---|---|---|---|---|---|---|---|
|TAT|CTG|TCT|CCG|CTG|GAT|ATT|ACC|GCG|GCA|CAG|TTT|AAG|GTG|CTC|TGC|1585|
|Tyr|Leu|Ser|Pro|Leu|Asp|Ile|Thr|Ala|Ala|Gln|Phe|Lys|Val|Leu|Cys| |
| | | |35| | | | |40| | | | |45| | | |

| | | | | | | | | | | | | | | | | |
|---|---|---|---|---|---|---|---|---|---|---|---|---|---|---|---|---|
|TCT|ATC|CGC|TGC|GCG|GCG|TGT|ATT|ACT|CCG|GTT|GAA|CTG|AAA|AAG|GTA|1633|
|Ser|Ile|Arg|Cys|Ala|Ala|Cys|Ile|Thr|Pro|Val|Glu|Leu|Lys|Lys|Val| |
| | |50| | | | |55| | | | |60| | | | |

| | | | | | | | | | | | | | | | | |
|---|---|---|---|---|---|---|---|---|---|---|---|---|---|---|---|---|
|TTG|TCG|GTC|GAC|CTG|GGA|GCA|CTG|ACC|CGT|ATG|CTG|GAT|CGC|CTG|GTC|1681|
|Leu|Ser|Val|Asp|Leu|Gly|Ala|Leu|Thr|Arg|Met|Leu|Asp|Arg|Leu|Val| |
| |65| | | | |70| | | | |75| | | | | |

| | | | | | | | | | | | | | | | | |
|---|---|---|---|---|---|---|---|---|---|---|---|---|---|---|---|---|
|TGT|AAA|GGC|TGG|GTG|GAA|AGG|TTG|CCG|AAC|CCG|AAT|GAC|AAG|CGC|GGC|1729|
|Cys|Lys|Gly|Trp|Val|Glu|Arg|Leu|Pro|Asn|Pro|Asn|Asp|Lys|Arg|Gly| |
|80| | | | |85| | | | |90| | | | |95| |

| | | | | | | | | | | | | | | | | |
|---|---|---|---|---|---|---|---|---|---|---|---|---|---|---|---|---|
|GTA|CTG|GTA|AAA|CTT|ACC|ACC|GGC|GGC|GCG|GCA|ATA|TGT|GAA|CAA|TGC|1777|
|Val|Leu|Val|Lys|Leu|Thr|Thr|Gly|Gly|Ala|Ala|Ile|Cys|Glu|Gln|Cys| |
| | | |100| | | | |105| | | | |110| | | |

| | | | | | | | | | | | | | | | | |
|---|---|---|---|---|---|---|---|---|---|---|---|---|---|---|---|---|
|CAT|CAA|TTA|GTT|GGC|CAG|GAC|CTG|CAC|CAA|GAA|TTA|ACA|AAA|AAC|CTG|1825|
|His|Gln|Leu|Val|Gly|Gln|Asp|Leu|His|Gln|Glu|Leu|Thr|Lys|Asn|Leu| |
| | | |115| | | | |120| | | | |125| | | |

| | | | | | | | | | | | | | | | | |
|---|---|---|---|---|---|---|---|---|---|---|---|---|---|---|---|---|
|ACG|GCG|GAC|GAA|GTG|GCA|ACA|CTT|GAG|TAT|TTG|CTT|AAG|AAA|GTC|CTG|1873|
|Thr|Ala|Asp|Glu|Val|Ala|Thr|Leu|Glu|Tyr|Leu|Leu|Lys|Lys|Val|Leu| |
| | |130| | | | |135| | | | |140| | | | |

| | | | | | | | | | | | | | | | |
|---|---|---|---|---|---|---|---|---|---|---|---|---|---|---|---|
|CCG|TAAACAAAAA|AGAGGT|ATG|ACG|ATG|TCC|AGA|CGC|AAT|ACT|GAC|GCT| | |1922|
|Pro| | |Met|Thr|Met|Ser|Arg|Arg|Asn|Thr|Asp|Ala| | | |
| | | |1| | | |5| | | | |10| | | |

| | | | | | | | | | | | | | | | | |
|---|---|---|---|---|---|---|---|---|---|---|---|---|---|---|---|---|
|ATT|ACC|ATT|CAT|AGC|ATT|TTG|GAC|TGG|ATC|GAG|GAC|AAC|CTG|GAA|TCG|1970|
|Ile|Thr|Ile|His|Ser|Ile|Leu|Asp|Trp|Ile|Glu|Asp|Asn|Leu|Glu|Ser| |
| | | | |15| | | | |20| | | | |25| | |

| | | | | | | | | | | | | | | | | |
|---|---|---|---|---|---|---|---|---|---|---|---|---|---|---|---|---|
|CCA|CTG|TCA|CTG|GAG|AAA|GTG|TCA|GAG|CGT|TCG|GGT|TAC|TCC|AAA|TGG|2018|
|Pro|Leu|Ser|Leu|Glu|Lys|Val|Ser|Glu|Arg|Ser|Gly|Tyr|Ser|Lys|Trp| |
| | | |30| | | | |35| | | | |40| | | |

| | | | | | | | | | | | | | | | | |
|---|---|---|---|---|---|---|---|---|---|---|---|---|---|---|---|---|
|CAC|CTG|CAA|CGG|ATG|TTT|AAA|AAA|GAA|ACC|GGT|CAT|TCA|TTA|GGC|CAA|2066|
|His|Leu|Gln|Arg|Met|Phe|Lys|Lys|Glu|Thr|Gly|His|Ser|Leu|Gly|Gln| |
| | |45| | | | |50| | | | |55| | | | |

| | | | | | | | | | | | | | | | | |
|---|---|---|---|---|---|---|---|---|---|---|---|---|---|---|---|---|
|TAC|ATC|CGC|AGC|CGT|AAG|ATG|ACG|GAA|ATC|GCG|CAA|AAG|CTG|AAG|GAA|2114|
|Tyr|Ile|Arg|Ser|Arg|Lys|Met|Thr|Glu|Ile|Ala|Gln|Lys|Leu|Lys|Glu| |
| |60| | | | |65| | | | |70| | | | | |

| | | | | | | | | | | | | | | | | |
|---|---|---|---|---|---|---|---|---|---|---|---|---|---|---|---|---|
|AGT|AAC|GAG|CCG|ATA|CTC|TAT|CTG|GCA|GAA|CGA|TAT|GGC|TTC|GAG|TCG|2162|
|Ser|Asn|Glu|Pro|Ile|Leu|Tyr|Leu|Ala|Glu|Arg|Tyr|Gly|Phe|Glu|Ser| |
|75| | | | |80| | | | |85| | | | |90| |

| | | | | | | | | | | | | | | | | |
|---|---|---|---|---|---|---|---|---|---|---|---|---|---|---|---|---|
|CAA|CAA|ACT|CTG|ACC|CGA|ACC|TTC|AAA|AAT|TAC|TTT|GAT|GTT|CCG|CCG|2210|
|Gln|Gln|Thr|Leu|Thr|Arg|Thr|Phe|Lys|Asn|Tyr|Phe|Asp|Val|Pro|Pro| |
| | | |95| | | | |100| | | | |105| | | |

```
CAT AAA TAC CGG ATG ACC AAT ATG CAG GGC GAA TCG CGC TTT TTA CAT      2258
His Lys Tyr Arg Met Thr Asn Met Gln Gly Glu Ser Arg Phe Leu His
        110                 115                 120

CCA TTA AAT CAT TAC AAC AGC TAGTTGAAAA CGTGACAACG TCACTGAGGC         2309
Pro Leu Asn His Tyr Asn Ser
        125

AATC ATG AAA CCA CTT TCA TCC GCA ATA GCA GCT GCG CTT ATT CTC TTT    2358
     Met Lys Pro Leu Ser Ser Ala Ile Ala Ala Ala Leu Ile Leu Phe
      1               5                  10                  15

TCC GCG CAG GGC GTT GCG GAA CAA ACC ACG CAG CCA GTT GTT ACT TCT      2406
Ser Ala Gln Gly Val Ala Glu Gln Thr Thr Gln Pro Val Val Thr Ser
                 20                  25                  30

TGT GCC AAT GTC GTG GTT GTT CCC CCA TCG CAG GAA CAC CCA CCG TTT      2454
Cys Ala Asn Val Val Val Val Pro Pro Ser Gln Glu His Pro Pro Phe
             35                  40                  45

GAT TTA AAT CAC ATG GGT ACT GGC AGT GAT AAG TCG GAT GCG CTC GGC      2502
Asp Leu Asn His Met Gly Thr Gly Ser Asp Lys Ser Asp Ala Leu Gly
         50                  55                  60

GTG CCC TAT TAT AAT CAA CAC GCT ATG TAGTTTGTTC TGGCCCCGAC            2549
Val Pro Tyr Tyr Asn Gln His Ala Met
     65                  70

ATCTCGGGGC TTATTAACTT CCCACCTTTA CCGCTTTACG CCACCGCAAG CCAAATACAT   2609
TGATATACAG CCCGGTCATA ATGAGCACCG CACCTAAAAA TTGCAGACCC GTTAAGCGTT   2669
CATCCAACAA TAGTGCCGCA CTTGCCAGTC CTACTACGGG CACCAGTAAC GATAACGGTG   2729
CAACCCGCCA GGTTTCATAG CGTCCCAGTA ACGTCCCCCA GATCCCATAA CCAACAATTG   2789
TCGCCACAAA CGCCAGATAC ATCAGAGACA AGATGGTGGT CATATCGATA GTAACCAGAC   2849
TGTGAATCAT GGTTGCGGAA CCATCGAGAA TCAGCGAGGC AACAAAGAAG GGAATGATTG   2909
GGATTAAAGC GCTCCAGATT ACCAGCGACA TCACCGCCGG ACGCGTTGAG TGCGACATGA   2969
TCTTTTTATT GAAGATGTTG CCACACGCCC AACTAAATGC TGCCGCCAGG GTCAACATAA   3029
AGCCGAGCAT CGCCACATGC TGACCGTTCA GACTATCTTC GATTAACACC AGTACGCCAA   3089
AAATCGCTAA GGCGATCCCC GCCAATTGTT TGCCATGCAG TCGCTCCCCG AAAGTAAACG   3149
CGCCAAGCAT GATAGTAAAA AACGCCTGTG CCTGTAACAC CAGCGAAGCC AGTCCAGCAG   3209
GCATACCGAA GTTAATGGCA CAAAAAGAA AAGCAAACTG CGCAAAACTG ATGGTTAATC   3269
CATACCCCAG CAGCAAATTC AGTGGTACTT TCGGTCGTGC GACAAAAAG ATAGCCGGAA   3329
AAGCGACCAG CATAAAGCGC AAACCGGCCA GCATCAGCGT GGCATGTTAT GAAGCCCCAC   3389
TTTGATGACC ACAAAATTTA GCCCCCATAC GACCACTACC AGTAGCGCCA ACACCCCATC   3449
TTTTCGCGAC ATTCTACCGC CTCTGAATTT CATCTTTTGT AAGCAATCAA CTTAGCTGAA   3509
TTTACTTTTC TTTAACAGTT GATTCGTTAG TCGCCGGTTA CGACGGCATT AATGCGCAAA   3569
TAAGTCGCTA TACTTCGGAT TTTTGCCATG CTATTTCTTT ACATCTCTAA AACAAACAT   3629
AACGAAACGC ACTGCCGGAC AGACAAATGA ACTTATCCCT ACGACGCTCT ACCAGCGCCC   3689
TTCTTGCCTC GTCGTTGTTA TTAACCATCG GACGCGGCGC TACCGTGCCA TTTATGACCA   3749
TTTACTTGAG TCGCCAGTAC AGCCTGAGTG TCGATCTAAT CGGTTATGCG ATGACAATTG   3809
CGCTCACTAT TGGCGTCGTT TTTAGCCTCG GTTTTGGTAT CCTGGCGGAT AAGTTCGACA   3869
AGAAACGCTA TATGTTACTG GCAATTACCG CCTTCGCCAG CGGTTTTATT GCCATTACTT   3929
TAGTGAATAA CGTGACGCTG GTTGTGCTCT TTTTTGCCCT CATTAACTGC GCCTATTCTG   3989
TTTTTGCTAC CGTGCTGAAA GCCTGGTTTG CCGACAATCT TTCGTCCACC AGCAAAACGA   4049
AAATCTTCTC AATCAACTAC ACCATGCTAA ACATTGGCTG ACCATCGGTC CGCCGCTCGG   4109
```

```
CACGCTGTTG GTAATGCAGA GCATCAATCT GCCCTTCTGG CTGGCAGCTA TCTGTTCCGC    4169
GTTTCCCATG CTTTTCATTC AAATTTGGGT AAAGCGCAGC GAGAAAATCA TCGCCACGGA    4229
AACAGGCAGT GTCTGGTCGC CGAAAGTTTT ATTACAAGAT AAAGCACTGT TGTGGTTTAC    4289
CTGCTCTGGT TTTCTGGCTT CTTTTGTAAG CGGCGCATTT GCTTCATGCA TTTCACAATA    4349
TGTGATGGTG ATTGCTGATG GGGATTTTGC CGAAAAGGTG GTCGCGGTTG TTCTTCCGGT    4409
GAATGCTGCC ATGGTGGTTA CGTTGCAATA TTCCGTGGGC CGCCGACTTA ACCCGGCTAA    4469
CATCCGCGCG CTGATGACAG CAGGCACCCT CTGTTCGTC ATCGGTCTGG TCGGTTTTAT     4529
TTTTTCCGGC AACAGCCTGC TATTGTGGGG TATGTCAGCT GCGGTATTTA CTGTCGGTGA    4589
AATCATTTAT GCGCCGGGCG AGTATATGTT GATTGACCAT ATTGCGCCGC CAGAAATGAA    4649
AGCCAGCTAT TTTTCCGCCC AGTCTTTAGG CTGGCTTGGT GCCGCGATTA ACCCATTAGT    4709
GAGTGGCGTA GTGCTAACCA GCCTGCCGCC TTCCTCGCTG TTTGTCATCT TAGCGTTGGT    4769
GATCATTGCT GCGTGGGTGC TGATGTTAAA AGGGATTCGA GCAAGACCGT GGGGGCAGCC    4829
CGCGCTTTGT TGATTTAAGT CGAACACAAT AAAGATTTAA TTCAGCCTTC GTTTAGGTTA    4889
CCTCTGCTAA TATCTTTCTC ATTGAGATGA AAATTAAGGT AAGCGAGGAA ACACACCACA    4949
CCATAAACGG AGGCAAATAA TGCTGGGTAA TATGAATGTT TTTATGGCCG TACTGGGAAT    5009
AATTTTATTT TCTGGTTTTC TGGCCGCGTA TTTCAGCCAC AAATGGGATG ACTAATGAAC    5069
GGAGATAATC CCTCACCTAA CCGGCCCCTT GTTACAGTTG TGTACAAGGG GCCTGATTTT    5129
TATGACGGCG AAAAAAAACC GCCAGTAAAC CGGCGGTGAA TGCTTGCATG GATAGATTTG    5189
TGTTTTGCTT TTACGCTAAC AGGCATTTTC CTGCACTGAT AACGAATCGT TGACACAGTA    5249
GCATCAGTTT TCTCAATGAA TGTTAAACGG AGCTTAAACT CGGTTAATCA CATTTTGTTC    5309
GTCAATAAAC ATGCAGCGAT TTCTTCCGGT TTGCTTACCC TCATACATTG CCCGGTCCGC    5369
TCTTCCAATG ACCACATCCA GAGGCTCTTC AGGAAATGCG CGACTCACAC CTGCTGTCAC    5429
GGTAATGTTG ATATGCCCTT CAGAATGTGT GATGGCATGG TTATCGACTA ACTGGCAAAT    5489
TCTGACACCT GCACGACATG CTTCTTCATC ATTAGCCGCT TTGACAATAA TGATAAATTC    5549
TTCGCCCCCG TAGCGATAAA CCGTTTCGTA ATCACGCGTC CAACTGGCTA AGTAAGTTGC    5609
CAGGGTGCGT AATACTACAT CGCCGATTAA ATGCCGTAG TATCATTAAC CAATTTAAAT     5669
CGGTCAATAT CCAACAACAT TAAATAAAGA TTCAGAGGCT CAGCGTTGCG TAACTGATGA    5729
TCAAAGGATT CATCAAGAAC CCGACGACCC GGCAATCCCG TCAAAACATC CATATTGCTA    5789
CGGATCGTCA GCAAATAAAT TTGTAATCG GTTAATGCCG CAGTAAAAGA AAGCAACCCC     5849
TCCTGAAAGG CGTCGAAATG CGCGTCCTGC CAGTGATTTT CAACAATAGC CAGCATTAAT    5909
TCCCGACCAC AGTTATGCAT ATGTTGATGG GCAGAATCCA TTAGCCGAAC GTAAGGTAAT    5969
TCATCGTTAT CGAGTGGCCC CAGATGATCA ATCCACCGAC CAAACTGGCA CAGTCCATAA    6029
GAATGGTTAT CCGTTATTTC TGGCTTACTG GCATCTCTCG CGACCACGCT GTGAAACATA    6089
CTCACCAGCC ACTGGTAGTG GGCATCGATA GCCTTATTGA GATTAACAA GATGGCATCA     6149
ATTTCCGTTG TCTTCTTGAT CATTGCCACT CCTTTTTCAC AGTTCCTTGT GCGCGCTATT    6209
CTAACGAGAG AAAAGCAAAA TTACGTCAAT ATTTTCATAG AAATCCGAAG TTATGAGTCA    6269
TCTCTGAGAT AACATTGTGA TTTAAAACAA AATCAGCGAA TAAAAAGTG TTTAATTCTG     6329
TAAATTACCT CTGCATTATC GTAAATAAAA GGATGACAAA TAGCATAACC CAATACCCTA    6389
ATGGCCCAGT AGTTCAGGCC ATCAGGCTAA TTTATTTTA TTTCTGCAAA TGAGTGACCC     6449
GAACGACGGC CGGCGCGCTT TTCTTATCCA GACTGCCACT AATGTTGATC ATCTGGTCCG    6509
```

-continued

```
GCTGAACTTC  TCGTCCATCA  AAGACGGCCG  CAGGAATAAC  GACATTAATT  TCACCGCTCT    6569
TATCGCGAAA  AACGTAACGG  TCCTCTCCTT  TGTGAGAAAT  CAAATTACCG  CGTAGTGAAA    6629
CCGAAGCGCC  ATCGTGCATG  GTTTTTGCGA  AATCAACGGT  CATTTTTTTT  GCATCATCGG    6689
TTCCGCGATA  GCCATCTTCT  ATTGCATGAG  GCGGCGGTGG  CGCTGCATCC  TGTTTTAAAC    6749
CGCCCTGGTC  ATCTGCCAAC  GCATAAGGCA  TGACAAGAAA  ACTTGCTAAT  ACAATGGCCT    6809
GAAATTTCAT  ACTAACTCCT  TAATTGCGTT  TGGTTTGACT  TATTAAGTCT  GGTTGCTATT    6869
TTTATAATTG  CCAAATAAGA  ATATTGCCAA  TTGTTATAAG  GCATTTAAAA  TCAGCCAACT    6929
AGCTGTCAAA  TATACAGAGA  ATTTAACTCA  CTAAAGTTAA  GAAGATTGAA  AAGTCTTAAA    6989
CATATTTTCA  GAATAATCGG  ATTTATATGT  TTGAAAATTA  TTATATTGGA  CGAGCATACA    7049
GAAAAGCAA   ATCACCTTTA  CATATAAAAG  CGTGGACAAA  AAACAGTGAA  CATTAATAGA    7109
GATAAAATTG  TACAACTTGT  AGATACCGAT  ACTATTGAAA  ACCTGACATC  CGCGTTGAGT    7169
CAAAGACTTA  TCGCGGATCA  ATTACGCTTA  ACTACCGCCG  AATCATGCAC  CGGCGGTAAG    7229
TTGGCTAGCG  CCCTGTGTGC  AGCTGAAGAT  ACACCCAAAT  TTTACGGTGC  AGGCTTTGTT    7289
ACTTTCACCG  ATCAGGCAAA  GATGAAAATC  CTCAGCGTAA  GCCAGCAATC  TCTTGAACGA    7349
TATTCTGCGG  TGAGTGAGAA  AGTGGCAGCA  GAAATGGCAA  CCGGTGCCAT  AGAGCGTGCG    7409
GATGCTGATG  TCAGTATTGC  CATTACCGGC  TACGGCGGAC  CGGAGGGCGG  TGAAGATGGT    7469
ACGCCAGCGG  GTACCGTCTG  GTTTGCGTGG  CATATTAAAG  GCCAGAACTA  CACTGCGGTT    7529
ATGCATTTTG  CTGGCGACTG  CGAAACGGTA  TTAGCTTTAG  CGGTGAGGTT  TGCCCTCGCC    7589
CAGCTGCTGC  AATTACTGCT  ATAACCAGGC  TGGCCTGGCG  ATATCTCAGG  CCAGCCATTG    7649
GTGGTGTTTA  TATGTTCAAG  CCACGATGTT  GCAGCATCGG  CATAATCTTA  GGTGCCTTAC    7709
CGCGCCATTG  TCGATACAGG  CGTTCCAGAT  CTTCGCTGTT  ACCTCTGGAA  AGGATCGCCT    7769
CGCGAAAACG  CAGCCCATTT  TCACGCGTTA  ATCGCCCTGC  TCAACAAACC  ACTGATAACC    7829
ATCATCGGCC  AACATTTGCG  TCCACAGATA  AGCGTAATAA  CCTGCAG                   7876
```

( 2 ) INFORMATION FOR SEQ ID NO:2:

( i ) SEQUENCE CHARACTERISTICS:
        ( A ) LENGTH: 157 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Met  Asp  Thr  Phe  Gly  Ile  Ser  Ile  Pro  Gly  Leu  Arg  Ile  Ala  Gly
 1              5                        10                       15

Gly  Leu  Ile  Val  Ala  Phe  Ile  Gly  Phe  Arg  Met  Leu  Phe  Pro  Gln  Gln
               20                       25                       30

Lys  Ala  Ile  Asp  Ser  Pro  Glu  Ala  Lys  Ser  Lys  Ser  Glu  Glu  Leu  Glu
               35                       40                       45

Asp  Glu  Pro  Ser  Ala  Asn  Ile  Ala  Phe  Val  Pro  Leu  Ala  Met  Pro  Ser
          50                       55                       60

Thr  Ala  Gly  Pro  Gly  Thr  Ile  Ala  Met  Ile  Ile  Ser  Ser  Ala  Ser  Thr
65                       70                       75                       80

Val  Arg  Gln  Ser  Ser  Thr  Phe  Ala  Asp  Trp  Val  Leu  Met  Val  Ala  Pro
                    85                       90                       95

Pro  Leu  Ile  Phe  Phe  Leu  Val  Ala  Val  Ile  Leu  Trp  Gly  Ser  Leu  Arg
                    100                      105                      110
```

-continued

| Ser | Ser | Gly | Ala | Ile | Met | Arg | Leu | Val | Gly | Lys | Gly | Gly | Ile | Glu | Ala |
|  | | 115 | | | | 120 | | | | | | 125 | | | |

| Ile | Ser | Arg | Leu | Met | Gly | Phe | Leu | Leu | Val | Cys | Met | Gly | Val | Gln | Phe |
| | | 130 | | | | 135 | | | | | 140 | | | | |

| Ile | Ile | Asn | Gly | Ile | Leu | Glu | Ile | Ile | Lys | Thr | Tyr | His |
| 145 | | | | | 150 | | | | | 155 | | |

( 2 ) INFORMATION FOR SEQ ID NO:3:

( i ) SEQUENCE CHARACTERISTICS:
        ( A ) LENGTH: 64 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

| Met | Leu | Asp | Leu | Phe | Lys | Ala | Ile | Gly | Leu | Gly | Leu | Val | Val | Leu | Leu |
| 1 | | | | 5 | | | | | 10 | | | | | 15 | |

| Pro | Leu | Ala | Asn | Pro | Leu | Thr | Thr | Val | Ala | Leu | Phe | Leu | Gly | Leu | Ala |
| | | | 20 | | | | 25 | | | | | 30 | | | |

| Gly | Asn | Met | Asn | Ser | Ala | Glu | Arg | Asn | Arg | Gln | Ser | Leu | Met | Ala | Ser |
| | | 35 | | | | 40 | | | | | 45 | | | | |

| Val | Tyr | Val | Phe | Ala | Ile | Met | Met | Val | Ala | Tyr | Tyr | Ala | Gly | Asn | Trp |
| | 50 | | | | 55 | | | | | 60 | | | | | |

( 2 ) INFORMATION FOR SEQ ID NO:4:

( i ) SEQUENCE CHARACTERISTICS:
        ( A ) LENGTH: 144 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Met | Lys | Ser | Thr | Ser | Asp | Leu | Phe | Asn | Glu | Ile | Ile | Pro | Leu | Gly | Arg |
| 1 | | | | 5 | | | | | 10 | | | | | 15 | |

| Leu | Ile | His | Met | Val | Asn | Gln | Lys | Lys | Asp | Arg | Leu | Leu | Asn | Glu | Tyr |
| | | | 20 | | | | 25 | | | | | 30 | | | |

| Leu | Ser | Pro | Leu | Asp | Ile | Thr | Ala | Ala | Gln | Phe | Lys | Val | Leu | Cys | Ser |
| | | 35 | | | | 40 | | | | | 45 | | | | |

| Ile | Arg | Cys | Ala | Ala | Cys | Ile | Thr | Pro | Val | Glu | Leu | Lys | Lys | Val | Leu |
| | 50 | | | | 55 | | | | | 60 | | | | | |

| Ser | Val | Asp | Leu | Gly | Ala | Leu | Thr | Arg | Met | Leu | Asp | Arg | Leu | Val | Cys |
| 65 | | | | | 70 | | | | | 75 | | | | | 80 |

| Lys | Gly | Trp | Val | Glu | Arg | Leu | Pro | Asn | Pro | Asn | Asp | Lys | Arg | Gly | Val |
| | | | | 85 | | | | | 90 | | | | | 95 | |

| Leu | Val | Lys | Leu | Thr | Thr | Gly | Gly | Ala | Ala | Ile | Cys | Glu | Gln | Cys | His |
| | | | | 100 | | | | | 105 | | | | | 110 | |

| Gln | Leu | Val | Gly | Gln | Asp | Leu | His | Gln | Glu | Leu | Thr | Lys | Asn | Leu | Thr |
| | | | 115 | | | | | 120 | | | | | 125 | | |

| Ala | Asp | Glu | Val | Ala | Thr | Leu | Glu | Tyr | Leu | Leu | Lys | Lys | Val | Leu | Pro |
| | | 130 | | | | 135 | | | | | 140 | | | | |

( 2 ) INFORMATION FOR SEQ ID NO:5:

( i ) SEQUENCE CHARACTERISTICS:
        ( A ) LENGTH: 129 amino acids
        ( B ) TYPE: amino acid
        ( D ) TOPOLOGY: linear (ii) MOLECULE TYPE: protein (xi) SEQUENCE DESCRIPTION: SEQ ID NO:5:

| Met | Thr | Met | Ser | Arg | Arg | Asn | Thr | Asp | Ala | Ile | Thr | Ile | His | Ser | Ile |
|---|---|---|---|---|---|---|---|---|---|---|---|---|---|---|---|
| 1 | | | | 5 | | | | | 10 | | | | | 15 | |

| Leu | Asp | Trp | Ile | Glu | Asp | Asn | Leu | Glu | Ser | Pro | Leu | Ser | Leu | Glu | Lys |
|---|---|---|---|---|---|---|---|---|---|---|---|---|---|---|---|
| | | | 20 | | | | | 25 | | | | | 30 | | |

| Val | Ser | Glu | Arg | Ser | Gly | Tyr | Ser | Lys | Trp | His | Leu | Gln | Arg | Met | Phe |
|---|---|---|---|---|---|---|---|---|---|---|---|---|---|---|---|
| | | | 35 | | | | | 40 | | | | | 45 | | |

| Lys | Lys | Glu | Thr | Gly | His | Ser | Leu | Gly | Gln | Tyr | Ile | Arg | Ser | Arg | Lys |
|---|---|---|---|---|---|---|---|---|---|---|---|---|---|---|---|
| | 50 | | | | | 55 | | | | | 60 | | | | |

| Met | Thr | Glu | Ile | Ala | Gln | Lys | Leu | Lys | Glu | Ser | Asn | Glu | Pro | Ile | Leu |
|---|---|---|---|---|---|---|---|---|---|---|---|---|---|---|---|
| 65 | | | | | 70 | | | | | 75 | | | | | 80 |

| Tyr | Leu | Ala | Glu | Arg | Tyr | Gly | Phe | Glu | Ser | Gln | Gln | Thr | Leu | Thr | Arg |
|---|---|---|---|---|---|---|---|---|---|---|---|---|---|---|---|
| | | | | 85 | | | | | 90 | | | | | 95 | |

| Thr | Phe | Lys | Asn | Tyr | Phe | Asp | Val | Pro | Pro | His | Lys | Tyr | Arg | Met | Thr |
|---|---|---|---|---|---|---|---|---|---|---|---|---|---|---|---|
| | | | 100 | | | | | 105 | | | | | 110 | | |

| Asn | Met | Gln | Gly | Glu | Ser | Arg | Phe | Leu | His | Pro | Leu | Asn | His | Tyr | Asn |
|---|---|---|---|---|---|---|---|---|---|---|---|---|---|---|---|
| | | 115 | | | | | 120 | | | | | 125 | | | |

Ser (2) INFORMATION FOR SEQ ID NO:6:

(i) SEQUENCE CHARACTERISTICS:
        (A) LENGTH: 72 amino acids
        (B) TYPE: amino acid
        (D) TOPOLOGY: linear (ii) MOLECULE TYPE: protein (xi) SEQUENCE DESCRIPTION: SEQ ID NO:6:

| Met | Lys | Pro | Leu | Ser | Ser | Ala | Ile | Ala | Ala | Ala | Leu | Ile | Leu | Phe | Ser |
|---|---|---|---|---|---|---|---|---|---|---|---|---|---|---|---|
| 1 | | | | 5 | | | | | 10 | | | | | 15 | |

| Ala | Gln | Gly | Val | Ala | Glu | Gln | Thr | Thr | Gln | Pro | Val | Val | Thr | Ser | Cys |
|---|---|---|---|---|---|---|---|---|---|---|---|---|---|---|---|
| | | | 20 | | | | | 25 | | | | | 30 | | |

| Ala | Asn | Val | Val | Val | Val | Pro | Pro | Ser | Gln | Glu | His | Pro | Pro | Phe | Asp |
|---|---|---|---|---|---|---|---|---|---|---|---|---|---|---|---|
| | | | 35 | | | | | 40 | | | | | 45 | | |

| Leu | Asn | His | Met | Gly | Thr | Gly | Ser | Asp | Lys | Ser | Asp | Ala | Leu | Gly | Val |
|---|---|---|---|---|---|---|---|---|---|---|---|---|---|---|---|
| | 50 | | | | | 55 | | | | | 60 | | | | |

| Pro | Tyr | Tyr | Asn | Gln | His | Ala | Met | | | | | | | | |
|---|---|---|---|---|---|---|---|---|---|---|---|---|---|---|---|
| 65 | | | | | 70 | | | | | | | | | | |

(2) INFORMATION FOR SEQ ID NO:7:

(i) SEQUENCE CHARACTERISTICS:
        (A) LENGTH: 266 amino acids
        (B) TYPE: amino acid
        (D) TOPOLOGY: linear (ii) MOLECULE TYPE: protein (xi) SEQUENCE DESCRIPTION: SEQ ID NO:7:

| Met | Leu | Ala | Gly | Leu | Arg | Phe | Met | Leu | Val | Ala | Phe | Pro | Ala | Ile | Phe |
|---|---|---|---|---|---|---|---|---|---|---|---|---|---|---|---|
| 1 | | | | 5 | | | | | 10 | | | | | 15 | |

| Phe | Val | Ala | Arg | Pro | Lys | Val | Pro | Leu | Asn | Leu | Leu | Leu | Gly | Tyr | Gly |
|---|---|---|---|---|---|---|---|---|---|---|---|---|---|---|---|
| | | | 20 | | | | | 25 | | | | | 30 | | |

| Leu | Thr | Ile | Ser | Phe | Ala | Gln | Phe | Ala | Phe | Leu | Phe | Cys | Ala | Ile | Asn |
|---|---|---|---|---|---|---|---|---|---|---|---|---|---|---|---|
| | | | 35 | | | | | 40 | | | | | 45 | | |

| Phe | Gly | Met | Pro | Ala | Gly | Leu | Ala | Ser | Leu | Val | Leu | Gln | Ala | Gln | Ala |
|---|---|---|---|---|---|---|---|---|---|---|---|---|---|---|---|
| | | | 50 | | | | | 55 | | | | | 60 | | |

-continued

| | | | | | | | | | | | | | | | |
|---|---|---|---|---|---|---|---|---|---|---|---|---|---|---|---|
| Phe 65 | Phe | Thr | Ile | Met | Leu 70 | Gly | Ala | Phe | Thr | Phe 75 | Gly | Glu | Arg | Leu | His 80 |
| Gly | Lys | Gln | Leu | Ala 85 | Gly | Ile | Ala | Leu | Ala 90 | Ile | Phe | Gly | Val | Leu 95 | Val |
| Leu | Ile | Glu | Asp 100 | Ser | Leu | Asn | Gly | Gln 105 | His | Val | Ala | Met | Leu 110 | Gly | Phe |
| Met | Leu | Thr 115 | Leu | Ala | Ala | Ala | Phe 120 | Ser | Trp | Ala | Cys | Gly 125 | Asn | Ile | Phe |
| Asn | Lys 130 | Lys | Ile | Met | Ser | His 135 | Ser | Thr | Arg | Pro | Ala 140 | Val | Met | Ser | Leu |
| Val 145 | Ile | Trp | Ser | Ala | Leu 150 | Ile | Pro | Ile | Ile | Pro 155 | Phe | Phe | Val | Ala | Ser 160 |
| Leu | Ile | Leu | Asp | Gly 165 | Ser | Ala | Thr | Met | Ile 170 | His | Ser | Leu | Val | Thr 175 | Ile |
| Asp | Met | Thr | Thr 180 | Ile | Leu | Ser | Leu | Met 185 | Tyr | Leu | Ala | Phe | Val 190 | Ala | Thr |
| Ile | Val | Gly 195 | Tyr | Gly | Ile | Trp | Gly 200 | Thr | Leu | Leu | Gly | Arg 205 | Tyr | Glu | Thr |
| Trp | Arg 210 | Val | Ala | Pro | Leu | Ser 215 | Leu | Leu | Val | Pro | Val 220 | Val | Gly | Leu | Ala |
| Ser 225 | Ala | Ala | Leu | Leu | Leu 230 | Asp | Glu | Arg | Leu | Thr 235 | Gly | Leu | Gln | Phe | Leu 240 |
| Gly | Ala | Val | Leu | Ile 245 | Met | Thr | Gly | Leu | Tyr 250 | Ile | Asn | Val | Phe | Gly 255 | Leu |
| Arg | Trp | Arg | Lys 260 | Ala | Val | Lys | Val | Gly 265 | Ser | | | | | | |

MULTIPLE ANTIBIOTIC RESISTANCE OPERON ASSAYS

RELATED APPLICATIONS

This application is a continuation-in-part of application Ser. No. 07/938,085 filed Aug. 28 1992, abandoned and entitled "Multiple Antibiotic Resistance Regulon Assays," the entire disclosure of which is incorporated herein by reference.

FIELD OF THE INVENTION

This invention relates generally to the field of antimicrobial therapy. In particular, the present invention relates to methods and products useful in inhibiting the growth of bacteria or other microbes. In addition, this invention relates to identifying loci in bacteria or other microbes which affect antibiotic or antimicrobial susceptibility and to the production of bacterial strains useful in the field of antimicrobial therapy.

BACKGROUND OF THE INVENTION

Antibiotic or antimicrobial substances have long been used to inhibit the growth of bacteria or other microbes and to treat bacterial or microbial infections in humans, other animals, and in tissue culture. The use of antibiotics or antimicrobials in a treatment regimen, however, has the undesirable effect of selecting for bacteria or other microbes which are resistant to those antibiotics or antimicrobials which are administered or applied. As a result, treatment regimens can be adversely affected or, in some cases, rendered ineffective. This necessitates a continual search for new antibiotics and antimicrobials.

Of particular interest is the discovery of bacteria which express a multiple antibiotic resistance phenotype (Mar). This phenotype entails simultaneous resistance to a multiplicity of antibiotics which are unrelated in chemical structure. The appearance of such bacteria and infections by such bacteria greatly increase the difficulty of identifying effective antibiotics and treating infections in humans or other animals.

Multiple antibiotic resistance in bacteria is most commonly associated with the presence of plasmids which contain one or more resistance genes, each encoding a single antibiotic resistance phenotype (Clewell 1981; Foster 1983). Multiple antibiotic resistance associated with the chromosome, however, has been reported in Klebsiella, Enterobacter, Serratia (Gutmann et al. 1985), Neisseria (Johnson and Morse 1988), and Escherichia (George and Levy 1983a).

Bacteria expressing the multiple antibiotic resistance phenotype can be isolated by selecting bacteria with a single antibiotic and then screening for cross-resistance to structurally unrelated antibiotics. For example, George and Levy initially described a chromosomal multiple antibiotic resistance system which exists in *Escherichia coli* and which can be selected by a single drug, e.g., tetracycline or chloramphenicol (George and Levy 1983a). In addition to resistance to the selective agents, the Mar phenotype includes resistance to structurally unrelated agents, including nalidixic acid, rifampin, penicillins, and cephalosporins (George and Levy 1983); more recently, resistance to the fluoroquinolones has been described (Cohen et al. 1989).

The expression of a Mar phenotype, conferring substantially increased, simultaneous and coordinated resistance to a multiplicity of structurally unrelated compounds, appears to involve coordinated changes in the expression of a multiplicity of loci. This has been demonstrated in Mar phenotype bacteria of the species *E. coli* (Cohen et al. 1989). Such coordinated control of the expression of a multiplicity of loci implies the existence of an operon which directly or indirectly regulates the expression of the multiplicity of loci directly responsible for the Mar phenotype. One locus in one such operon was identified in *E. coli* and named marA by George and Levy (George and Levy 1983b).

Prior to the present invention, however, no multiple antibiotic resistance (mar) operon had been isolated or cloned. In addition, no mar operon had been characterized as to its structure and operation so as to enable the use of such an operon or its fragments for diagnostic, therapeutic or experimental purposes. Finally, the several other contributions to the field of antibacteriology in the claims were unavailable to those skilled in the art prior to the present invention.

SUMMARY OF THE INVENTION

The present invention relates generally to developing and evaluating antibiotic treatments effective against bacteria possessing a multiple antibiotic resistance (mar) operon. Because the expression of such an operon causes bacteria to become simultaneously resistant to a multiplicity of structurally unrelated antibiotics, it is a general object of the present invention to provide methods and compositions useful in combating bacteria possessing a mar operon or exhibiting a Mar phenotype. It is one particular object of the present invention to provide tests for compositions which are effective against bacteria expressing a Mar phenotype but which do not induce the expression of a mar operon, or which inhibit the expression of a mar operon. To this end, it is also an object of the present invention to provide cloned nucleotide sequences, as well as bacterial cells expressing such sequences, which are useful in performing such tests and in investigating bacterial multiple antibiotic resistance operons.

The present invention provides cloned bacterial mar operons and cloned fragments thereof. In particular, a cloned repressor locus and a cloned activator locus of a mar operon, as well as cloned loci encoding anti-sense transcripts to the repressor and activator loci, are provided. Using such clones, substantially pure repressor protein and substantially pure activator protein are provided. In addition, using such clones, isolated nucleotide sequences, either sense or anti-sense to those loci, are provided. These sequences are useful as probes for substantially homologous loci in other species including bacteria, fungi, parasites, and animal cells and are useful for altering the expression of a Mar phenotype in bacteria, either by encoding repressor or activator proteins or by encoding anti-sense transcripts which inhibit the expression of either a mar repressor or mar activator locus.

The present invention also provides cloned nucleotide sequences in which the regulatory region of a mar operon has been operably joined to a marker locus. Such sequences are useful in assaying the effect of compositions on the transcription of a mar operon.

The present invention also provides methods for evaluating the antibiotic effectiveness of compositions by assaying their effects upon the transcription of a mar operon or upon the activity of proteins encoded by a mar operon. In particular, the present invention provides methods for assessing the ability or inability of a composition to inhibit the activity of a mar repressor, to enhance the activity of a mar repressor, or to inhibit the activity of a mar activator.

Compositions which enhance the activity of a mar repressor or inhibit the activity of a mar activator will be useful either alone or in combination with antibiotics to combat bacteria. A method of treatment for bacterial infections using a combination of such compositions along with antibiotics is thus provided.

The present invention also provides methods for evaluating the antibiotic effectiveness of compositions by assaying their effects on bacteria in which the expression of a mar operon has been substantially increased and on bacteria in which the expression of a mar operon has been substantially decreased. To this end, methods of producing such bacteria and such bacteria themselves are provided.

The present invention also provides tests for identifying loci in bacteria which are subject to regulation, directly or indirectly, by a mar operon. Because such loci may be involved in the expression of a Mar phenotype, their identification will be useful in developing antibiotic compositions which affect the products or expression of those loci.

The present invention also provides cloned bacterial loci and fragments thereof which are subject to mar operon regulation and which, therefore, form part of a mar regulon. Using such clones, substantially pure protein encoded by these loci are provided. In addition, using such clones, isolated nucleotide sequences, either sense or anti-sense to these loci, are provided. These sequences are useful as probes for substantially homologous loci in other species including bacteria, fungi, parasites, and animal cells and for altering the expression of a Mar phenotype in bacteria.

BRIEF DESCRIPTION OF THE DRAWING

FIG. 1 is a schematic diagram of the first 3.5 kb of SEQ ID NO: 1.

DETAILED DESCRIPTION OF THE INVENTION

In the description that follows, a number of terms used in biochemistry, molecular biology and recombinant DNA technology are extensively utilized. In addition, certain new terms are introduced for greater ease of exposition and to more clearly and distinctly point out the subject matter of the invention. In order to provide a clear and consistent understanding of the specification and claims, including the scope to be given such terms, the following definitions are provided.

By a "locus" is understood a nucleotide sequence encoding a peptide. A locus consists of a start codon, a stop codon and at least one codon encoding an amino acid residue in between. Typically, a locus is transcribed to produce an mRNA transcript and that transcript is translated to produce a peptide.

By "regulatory region" is understood a nucleotide sequence involved in regulating the transcription of one or more loci. Regulatory regions will include a promoter sequence at which an RNA polymerase may bind and, typically, an operator sequence which may be bound by a repressor protein. Additionally, regulatory regions may include enhancers of transcription.

By "operon" is understood one or more loci operably joined to a regulatory region such that, under appropriate conditions, an RNA polymerase may bind to a promoter sequence in the regulatory region and proceed to transcribe the loci. The loci within an operon share a common regulatory region and, therefore, are substantially regulated as a unit. Amongst the loci in an operon may be a repressor locus which encodes a repressor protein which, under appropriate conditions, binds to the operator of the operon so as to substantially decrease expression of the loci in the operon.

By "regulon" is understood two or more loci in two or more different operons whose expression is regulated by a common repressor or activator protein. A "first" operon may, for example, encode a repressor protein which, under appropriate conditions, binds to the operators of two or more different operons so as to substantially inhibit transcription of the loci within those operons. Or, a "first" operon may encode an activator protein which interferes with the activity of one or more repressors of two or more different operons so as to substantially increase the transcription of the loci within those operons. Alternatively, a "first" operon may encode a protein which affects the translation or activity of proteins encoded by one or more loci in two or more different operons. In each of these cases, the latter operons form a regulon which is regulated by a common protein product of the "first" operon.

By a "bacterial multiple antibiotic resistance regulon" ("mar regulon") is understood a regulon encoding a multiplicity of protein products which are regulated in expression or activity by a common protein product and which can cause a substantial increase in resistance to a multiplicity of antibiotics, at least some of which antibiotics are unrelated structurally.

By a "bacterial multiple antibiotic resistance operon" ("mar operon") is understood a bacterial operon which, by its expression, affects the expression of two or more different operons which form a mar regulon. That is, by a "bacterial multiple antibiotic resistance operon" is understood a bacterial operon which, by its expression, affects the expression of two or more loci in two or more different operons, or which affects the activity of two or more protein products of such loci, so as to substantially increase resistance to a multiplicity of antibiotics, at least some of which are structurally unrelated. Amongst the loci in a bacterial multiple antibiotic resistance operon, there is at least one locus encoding an activator of a bacterial multiple antibiotic resistance regulon. Amongst the loci in a bacterial multiple antibiotic resistance operon, there may also be a locus encoding a repressor of the bacterial multiple antibiotic resistance operon. The mar operon of *E. coli* includes the marO region and marR, marA and marB loci disclosed herein and is, therefore, also referred to as the marRAB operon.

By a "repressor of a bacterial multiple antibiotic resistance operon" ("mar repressor") is understood a protein which, under appropriate conditions, binds to the operator of the operon so as to substantially inhibit the transcription of the operon. Such repressor proteins are encoded by repressor loci of bacterial multiple antibiotic resistance operons.

By an "activator of a bacterial multiple antibiotic resistance regulon" ("mar activator") is understood a protein encoded by a locus within a mar operon which, under appropriate conditions, affects the expression of two or more loci in a mar regulon or the activity of two or more proteins from such a regulon so as to cause expression of a bacterial multiple antibiotic resistance phenotype.

By an "enhancer of a bacterial multiple antibiotic resistance regulon" ("mar enhancer") is understood a protein encoded by a locus within a mar operon which, under appropriate conditions, enhances the expression or activity of a mar activator so as to increase expression of a bacterial multiple antibiotic resistance phenotype.

By a "bacterial multiple antibiotic resistance phenotype" ("Mar phenotype") is understood simultaneous and coordinated resistance to a multiplicity of antibiotics, at least some of which are structurally unrelated, which is substantially increased relative to typical or wild-type bacteria. The antibiotic resistance is simultaneous and coordinated in that the resistance to the multiplicity of antibiotics increases or arises simultaneously and may be decreased or lost simultaneously.

By an "inducer of a bacterial multiple antibiotic resistance operon" ("mar inducer") is understood a chemical composition or moiety which, under appropriate conditions, directly or indirectly inhibits the binding of a repressor of a mar operon to the regulatory region of that operon so as to substantially increase the expression of that operon and, consequently, the expression of a multiple antibiotic resistance phenotype.

By a "marker locus" is understood a locus whose expression is easily assayed. A marker locus is typically a locus encoding an enzyme and the assay may include a substance which changes color in the presence of a product of the enzyme's activity. Alternatively, a marker locus may encode a protein which directly or indirectly affects a visually apparent phenotype of an organism such as color or colony type in bacteria. Alternatively, a marker locus may encode a protein which directly or indirectly confers substantial resistance to, sensitivity to, or dependence upon a particular composition.

By "expression" of a locus is understood the transcription of the locus to produce mRNA and the translation of the mRNA transcript to produce a peptide. By "substantially decreased expression of a locus" is understood a decrease in detectable expression of its mRNA transcript and/or protein product of at least about 10% and preferably more than 25% of the previous level. By "substantially increased expression of a locus" is understood an increase in the level of its mRNA transcript and/or protein product of at least about 10% and preferably about 25% of the previous level.

By an "operable" locus is understood a locus capable of being transcribed under appropriate conditions in vivo or in vitro. A locus or nucleotide sequence is "operably joined" to a regulatory region if, under appropriate conditions, an RNA polymerase may bind to the promoter of the regulatory region and proceed to transcribe the locus or nucleotide sequence in an appropriate reading frame. A locus or nucleotide sequence operably joined to a regulatory region is operable.

A coding sequence and a regulatory region are said to be operably joined when they are covalently linked in such a way as to place expression of the coding sequence under the influence or control of the regulatory sequence. Two DNA sequences are said to be operably joined if induction of the promoter function of one results in the transcription of an mRNA sequence corresponding to the coding sequences of the other. If it is desired that the RNA transcript be translated into a protein or polypeptide, there are further considerations. A coding sequencing which is to be translated into a protein or polypeptide is said to be operably joined to a regulatory region if induction of the promoter results in the transcription of an mRNA transcript corresponding to the coding sequences and if the nature of the linkage between the two DNA sequences does not (1) result in the introduction of a frame-shift mutation, (2) interfere with the ability of the regulatory sequences to initiate and promote the transcription of the coding sequences, or (3) interfere with the ability of the mRNA template to be translated into a functional protein. Thus, a regulatory region would be operably joined to a DNA sequence if the promoter were capable of effecting transcription of that DNA sequence such that the resulting transcript might be translated into a functional protein or polypeptide.

If it is not desired that the coding sequence be eventually expressed as a protein or polypeptide, as in the case of anti-sense RNA expression, there is no need to ensure that the coding sequences and regulatory region are joined without a frame-shift. Thus, a coding sequence which need not be eventually expressed as a protein or polypeptide is said to be operably joined to a regulatory region if induction of promoter function results in the transcription of an mRNA sequence corresponding to the coding sequences.

The precise nature of the regulatory region needed for gene expression may vary between species or cell types, but shall in general include, as necessary, 5' non-transcribing and 5' non-translating (non-coding) sequences involved with initiation of transcription and translation respectively, such as a TATA box, capping sequence, CAAT sequence, and the like. Especially, such 5' non-transcribing regulatory sequences will include a region which contains a promoter for transcriptional control of the operably joined coding sequences. Such regulatory regions may also include enhancer sequences or upstream activator sequences, as desired.

By "homology" of nucleotide sequences is understood a correlation in the nucleotide composition and ordering of the sequences. If the composition and ordering of the nucleotides are the same or substantially the same, the sequences are characterized by "sense" homology. If the composition and ordering of the nucleotides of the sequences are substantially complementary such that the sequences may, under appropriate conditions, hydrogen bond in the manner of complementary strands of DNA, the sequences are characterized by "anti-sense" homology. Sequences characterized by sense homology to the mRNA transcript of a locus may, under appropriate conditions, bind to the DNA of that locus so as to inhibit further transcription. Sequences characterized by anti-sense homology to the mRNA transcript of a locus may, under appropriate conditions, bind to the DNA of that locus so as to inhibit further transcription or bind to the mRNA transcript of that locus so as to inhibit translation.

Two nucleotide sequences are substantially homologous if one of them or its anti-sense complement can bind to the other under strict hybridization conditions so as to distinguish that strand from all or substantially all other sequences in a cDNA or genomic library. Alternatively, one sequence is substantially homologous to another if it or its anti-sense complement is useful as a probe in screening for the presence of its homologous DNA or RNA sequence under strict hybridization conditions. "stringent hybridization" conditions is a term of art understood by those of ordinary skill in the art. For any given nucleotide sequence, stringent hybridization conditions are those conditions of temperature and buffer solution which will permit hybridization of that nucleotide sequence to its complementary sequence and not to substantially different sequences. The exact conditions which constitute "stringent" conditions, depend upon the length of the nucleotide sequence and the frequency of occurrence of subsets of that sequence within other non-identical sequences. By varying hybridization conditions from a level of stringency at which no hybridization occurs to a level at which hybridization is first observed, one of ordinary skill in the art can, without undue experimentation, determine conditions which will allow a given sequence to hybridize only with perfectly complementary sequences. Hybridization conditions which permit hybridization to imperfectly complementary sequences are employed to isolate nucleotide sequences which are allelic to or evolutionary homologs of any given sequence. Suitable ranges of such stringency conditions are described in Krause, M. H. and S. A. Aaronson, *Methods in Enzymology*, 200:546–556 (1991). By a sequence which is "substantially homologous" to some specified sequence is understood a sequence which will hybridize to the specified sequence, its allelic variants and evolutionary homologs under stringent hybridization conditions so as to distinguish those sequences from non-allelic, non-homologous sequences.

By an "anti-sense locus" is understood a locus which encodes an mRNA transcript characterized by substantial anti-sense homology to the mRNA encoded by a specified locus. An anti-sense locus to an activator locus of a bacterial multiple antibiotic resistance operon, for example, will encode an mRNA transcript characterized by substantial anti-sense homology to the mRNA transcript encoded by the activator locus. The anti-sense mRNA may bind to the DNA of the activator locus so as to inhibit further transcription or it may bind to the mRNA transcript of the activator locus so as to inhibit translation.

By "antibiotic" is understood a chemical composition or moiety which decreases the viability or which inhibits the growth or reproduction of microbes. As used in this disclosure, for simplicity of exposition, antibiotics are intended to embrace antibacterial, antiviral, antifungal and, generally, antimicrobial compositions.

By an "isolated" nucleotide sequence is understood a nucleotide sequence which has been: (1) amplified in vitro by, for example, polymerase chain reaction (PCR); (2) recombinantly produced by cloning; (3) purified, as by cleavage and gel separation; or (4) synthesized by, for example, chemical synthesis. An isolated nucleotide sequence is one which is readily manipulable by recombinant DNA techniques well known in the art. Thus, a nucleotide sequence contained in a vector in which 5' and 3' restriction cytes are known or for which polymerase chain reaction (PCR) primer sequences have been disclosed is considered isolated, but a nucleotide sequence existing in its native state in its natural host is not. An isolated nucleotide sequence may be substantially purified, but need not be. For example, a nucleotide sequence that is isolated within a cloning or expression vector is not pure in that it may comprise only a tiny percentage of the material in the cell in which it resides. Such a nucleotide sequence is, however, isolated as the term is used herein because it is readily manipulable by standard techniques of recombinant DNA technology known to those of ordinary skill in the art.

By "fragment" is understood a unique fragment, a substantially characteristic fragment, or a functional fragment as defined below.

As used herein, a "unique fragment" of a protein or nucleotide sequence is a substantially characteristic fragment not currently known to occur elsewhere in nature (except in allelic or allelomorphic variants). A unique fragment will generally exceed 15 nucleotides or 5 amino acid residues. One of ordinary skill in the art can substantially identify unique fragments by searching available computer databases of nucleotide and protein sequences such as Genbank (Los Alamos National Laboratories, USA) or the National Biomedical Research Foundation database. A unique fragment is particularly useful, for example, in generating monoclonal antibodies or in screening DNA or cDNA libraries.

A "substantially characteristic fragment" of a molecule, such as a protein or nucleotide sequence, is meant to refer to any portion of the molecule sufficiently rare or sufficiently characteristic of that molecule so as to identify it as derived from that molecule or to distinguish it from a class of related molecules. A single amino acid or nucleotide cannot be a substantially characteristic fragment. A substantially characteristic fragment of a nucleotide sequence would have utility as a probe in identifying the entire nucleotide sequence from which it is derived within a sample of total genomic or DNA. A substantially characteristic fragment of a protein would have utility in generating antibodies which would distinguish the entire protein from which it is derived from a mixture of many proteins. It is within the knowledge and ability of one ordinarily skilled in the art to recognize, produce and use substantially characteristic fragments as, for example, probes for screening DNA libraries or epitopes for generating antibodies.

By a "functional fragment" of a molecule is understood a fragment retaining or possessing substantially the same biological activity as the intact molecule. For example, a functional fragment of a promoter sequence is a nucleotide sequence which retains or possesses the ability to initiate and promote transcription of a downstream nucleotide sequence by an RNA polymerase. Similarly, a functional fragment of a repressor protein is a fragment which retains or possesses the ability to bind to an operator sequence of a regulatory region so as to substantially inhibit the ability of an RNA polymerase to transcribe the downstream coding sequences. In all instances, a functional fragment of a molecule retains at least 10% and at least about 25% of the biological activity of the intact molecule.

The present invention in one aspect provides cloned bacterial multiple antibiotic resistance operons. A bacterial mar operon may be most easily isolated and cloned from any of a number of species using the nucleotide sequences disclosed herein. Absent the use of the nucleotide sequences disclosed herein, a mar operon may still be isolated using the following procedures.

A strain of bacteria is first subjected to selection on solid or in fluid medium containing an antibiotic. The selection may be step-wise, with incrementally increasing concentrations of the antibiotic. Amongst the surviving cells will be some spontaneous mar operon mutants which express the Mar phenotype. Such Mar mutants may be identified by their cross-resistance to a multiplicity of antibiotics which are structurally unrelated to the selective agent. The approximate map position of the operon may then be determined by mating transfer experiments which are well known in the art.

The Mar phenotype bacteria may then be mutagenized with a transposon and cells reverting to the wild-type (non-Mar) phenotype can be isolated by selecting for antibiotic susceptibility on replicated plates. A high percentage of the revertants will be the result of inactivation of the mar operon by insertion of the transposon within the operon. Using a restriction enzyme known to recognize a site within the transposon, fragments of the transposon joined to segments of chromosomal DNA can be cloned into vectors. These clones may, in turn, be used to probe a genomic library of the cells to identify clones bearing at least a fragment of the mar operon. Finally, these clones may be tested for their ability to complement cells in which there is a large deletion around the approximate mar map position. Clones capable of providing mar operon activity to the deletants will contain an operable mar operon and may be sequenced by standard techniques. This technique was used to identify the mar operon of *E. coli* (See Example 1). Given the nucleotide sequence of the mar operon of *E. coli*, however, such a technique is not necessary for isolating substantially homologous operons in other species.

In one particular aspect, therefore, the present invention provides the cloned wild-type mar operon of E. coli. One sequence containing a wild-type mar operon is presented as SEQ ID NO: 1. This sequence has been entered into GenBank with Accession #M96235 and corresponds to the 7.8 kbp fragment isolated in Example 1. This sequence or any fragment of it may, of course, be cloned into any of a number of vectors which are known to those of ordinary skill in the art.

Conservative variations on the DNA sequence SEQ ID NO: 1 exist which will have no substantial effect on the expression of the operon. The substitution of synonymous codons is one example. A small deletion or insertion which does not disrupt the reading frame is another. Substantially homologous sequences from a mar operon in a species other than E. coli are another example, particularly when such operons are identified by the methods and compositions disclosed herein. Such conservative variations would be obvious to one of ordinary skill in the art and fall within the spirit and scope of the claims.

The sequence of SEQ ID NO: 1 includes three regions. These regions are depicted in FIG. 1.

Analysis of this sequence reveals a regulatory region with promoter-operator sequences, designated marO. The marO sequence extends from approximately nucleotide positions 1234 to 1444 of SEQ ID NO: 1 between Region I and Region II. Transcription of Region I proceeds leftward from marO on the DNA strand complementary to SEQ ID NO: 1 whereas transcription of Region II proceeds rightward from marO on the DNA strand depicted as SEQ ID NO: 1. The marO sequence includes two pairs of direct repeat (DR) elements. DR-1, 15 bp long with one mismatch at position 9 of the DR (TACTTGCC[T/A]GGGCAA), begins at position 1390 of SEQ ID NO: 1 and its partner, DR-1', begins at position 1425. DR-1' is part of an imperfect palindrome starting at position 1423 (ATTACTTGCCAGGGCAACTAAT) and DR-1 is part of a similar shorter palindrome. A second DR (DR-2 and DR-2') of 9 bp (GCAACTAAT) flanks on both sides and partly overlaps the downstream part of DR-1'. For Region I, marO includes a promoter with −10 and −35 E. coli consensus sequences at about nucleotide positions 1350 and 1370, respectively, and/or at about positions 1275 and 1301, respectively. For Region II, marO includes a promoter with nearly perfect −10 and −35 E. coli consensus sequences at about nucleotide positions 1408 and 1384, respectively.

Region II includes four potential open reading frames (ORFs) designated ORF 125, ORF 144, ORF 129 and ORF 72.

ORF 125 begins with an ATG start codon at nucleotide positions 1502–1504 of SEQ ID NO: 1 and ends with a TAA stop codon at positions 1877–1879, and encodes a protein of 125 amino acid residues. Based upon sequencing of Mar mutants, ORF 125 was originally considered the mar repressor locus but, based on fusion-protein studies of binding to marO, described more fully below (See Example 10), ORF 125 does not encode the full mar repressor.

ORF 144 begins with a GTG start codon at nucleotide positions 1445–1447 of SEQ ID NO: 1, ends with the same TAA stop codon as ORF 125 at positions 1877–1879 (thereby encompassing all of ORF 125). ORF 144 encodes the full mar repressor (144 amino acid residues) and is, therefore, designated the marR locus. The mar repressor regulates not only transcription of Region II (in which marR is found) but also has a regulatory function for Region I. The protein, MarR, encoded by ORF 144 is disclosed as SEQ ID NO: 4. Note that the first GTG codon is translated as a Met residue.

The second locus of Region II, marA, corresponds to ORF 129 and encodes a protein of 129 amino acids, designated the mar activator. The marA locus extends from nucleotide 1893 of SEQ ID NO: 1 to nucleotide 2282. The mar activator (MarA) is a 13 kDa polypeptide that shows strong similarity to the family of positive regulators that includes regulators of carbohydrate metabolism in Escherichia coli (AraC, RhaR, RhaS, and MelR), Erwinia corotovora (AraC), and Pseudomonas putida (XylS); virulence in Yersinia enterocolitica (VirF) and E. coli (Rns); and oxidative stress response in E. coli (SoxS) (Cohen, Hachler and Levy, 1993). For example, the MarA protein is strongly similar (42% identical, 65% similar) to the SoxS protein which activates the soxRS regulon genes (Amabile-Cuevas and Demple, 1991). The protein, MarA, encoded by ORF 129 is disclosed as SEQ ID NO: 5

The third locus of Region II, marB, corresponds to ORF 72 and encodes a protein of 72 amino acids, designated the mar enhancer. The marB locus extends from nucleotide 2314 of SEQ ID NO: 1 to nucleotide 2531. The marB locus is necessary for expression of the full Mar phenotype although its precise mode of action remains unclear. The protein, MarB, encoded by ORF 72 is disclosed as SEQ ID NO: 6.

The marO region and the marR, marA and marB loci form the mar operon, or marRAB operon, of E. coli. The mar repressor acts to repress expression of the operon by binding at marO. The mar activator acts directly or indirectly to alter the expression of other operons, loci or proteins which are part of the mar regulon and which are directly involved with the expression of the Mar phenotype. The mar enhancer augments the expression of the Mar phenotype. In addition to these E. coli homologs of the bacterial mar operon, hybridization studies, disclosed more fully below, indicate that substantially homologous sequences are included in the genomes of many other bacterial species and that bacterial mar operons share a common ancestry and evolutionarily conserved structure. In light of the present disclosure, one of ordinary skill in the art may readily isolate the mar operons of other species.

Transcription from marO through Region I (leftward with respect to SEQ ID NO: 1 on the complementary DNA strand) proceeds through two open reading frames designated ORF 64 and ORF 156/157. ORF 64 begins with an ATG start codon complementary to the TAC found (reading leftward) at positions 1233–31 of SEQ ID NO: 1 and ends with a TGA stop codon complementary to the ACT at positions 1041–1039. ORF 156/157 begins either at the GTG complementary to the CAC at positions 1042–1040 or at the ATG complementary to the TAC at positions 1039–1037, and ends with the TAA complementary to the ATT at positions 571–569 of SEQ ID NO: 1. The protein encoded by ORF 157 is disclosed as SEQ ID NO: 2. Note that the first GTG is translated as Met.

Although the functions of the Region I proteins are not yet known, they are part of the mar regulon and function directly in the phenotypic expression of Mar. Mar phenotype mutants produce somewhat higher levels of Region I mRNA than wild-type cells and clearly more in the presence of tetracycline. In addition, deletants without both Region I and Region II show 2–3 fold lower antibiotic resistance than deletants without only Region II (see Example 11).

Region III contains a single significant open reading frame, ORF 266, which encodes a protein of 266 residues. ORF 266 is transcribed in the opposite (leftward) direction from the loci of Region II and from the strand of DNA complementary to SEQ ID NO: 1. ORF 266 begins with an ATG start complementary to the TAC at positions 3363–3361 of SEQ ID NO: 1 and ends with the TAA stop codon complementary to the ATT at positions 2565–2563. The function of the ORF 266 protein is currently unknown and the level of Region III MRNA transcripts are not detectably affected by the Mar status of cells or the presence of tetracycline. The protein encoded by ORF 266 is disclosed as SEQ ID NO: 7.

The present invention thus provides cloned fragments of these various regions including regulatory regions, protein coding sequences or both. Particular examples include cloned mar regulatory sequences and cloned mar repressor, mar activator, and mar enhancer loci of bacterial mar operons. The particular examples provided are the cloned *E. coli* maro sequences and marR, marA, and marB loci. In addition, the cloned *E. coli* ORF 64 and ORF 157 sequences are provided. Such loci are cloned preferably so as to be operably joined to a regulatory region so that they may be expressed under conditions wherein the regulatory region is not blocked by a repressor. The loci may be operably joined to a mar regulatory region or to other regulatory regions depending upon the desired manner of regulation and levels of expression. In addition, the invention provides vectors containing an operably cloned mar repressor locus without a mar activator locus and with or without a mar enhancer locus (see Example 2), an operably cloned mar activator locus without a mar repressor locus and with or without a mar enhancer locus (see Example 3), and an operably cloned mar enhancer locus without a mar repressor locus and with or without a mar activator locus (see Example 3). Given the sequences disclosed herein, as well as the methods provided for identifying substantially homologous mar operons in other species, one of ordinary skill in the art is enabled to produce such cloned loci. In addition, anti-sense clones of these loci can be as easily produced and are also an aspect of the present invention.

Conservative variations on SEQ ID NO: 1 exist which will have no substantial effect on the expression of these loci. The substitution of synonymous codons is one example. A small deletion or insertion which does not disrupt the reading frame is another. A sequence from a mar operon in a species other than *E. coli* is another example, particularly when such a sequence is identified by the methods and compositions disclosed herein. Such conservative variations would be obvious to one of ordinary skill in the art and fall within the spirit and scope of the claims.

The present invention also provides probes useful in identifying mar operons in species other than *E. coli*. A cloned mar operon or cloned fragment of a mar operon from one species can be used to screen a DNA library of another species to identify potential mar operons by methods which are known to those of ordinary skill in the art. DNA homologous to marRAB has been found among many members of the Enterobacteriaceae including Klebsiella (Cohen, Yan and Levy, 1993). Similarly, induction of the Mar phenotype by salicylate and acetyl salicylate has been commonly observed among 58 clinical enteric isolates tested (Foulds and Rosner, personal communication). In Klebsiella, Serratia and *Pseudomonas cepacia*, the salicylate decreased the presence of OmpF-like outer membrane porins (Burns and Clark, 1992; Sawai, Hirano and Yamaguchi, 1987). Furthermore, in Klebsiella, salicylates increased resistance to various antibiotics (including β-lactams and tetracycline), decreased resistance to aminoglycosides and decreased the amounts of capsular polysaccharide (Domenico, Hopkins and Cunha, 1990; Domenico, Landolphi and Cunha, 1991). This indicates that mar operons are involved in salicylate induction of Mar phenotypes in many enterobacteria.

In one preferred embodiment, the cloned *E. coli* mar operon disclosed as SEQ ID NO: 1 or a fragment thereof is used to produce probes which are radioactively labeled with $^{32}$P (see Example 4). In a particularly preferred embodiment, the probe is a fragment of the *E. coli* marA or marR locus and, most preferably, a unique fragment. Such probes have been found to hybridize with DNA extracted from a wide variety of bacteria and may reveal an ancient and evolutionarily highly conserved family of loci and operons in species extending beyond bacteria.

Conservative variations on the disclosed DNA sequence exist which will not substantially impair the effectiveness of such probes. The substitution of a small percentage of the bases, small insertions, and small deletions are examples. Sequences from a mar operon in a species other than *E. coli* are another example, particularly when such operons are identified by the methods and compositions disclosed herein. Such conservative variations would be obvious to one of ordinary skill in the art and fall within the spirit and scope of the claims.

The present invention in another aspect provides substantially pure mar repressor protein, substantially pure mar activator protein and substantially pure mar enhancer protein. In particular, the invention provides substantially pure *E. coli* mar repressor protein, substantially pure *E. coli* mar activator protein and substantially pure *E. coli* mar enhancer protein (see Example 5). Substantially pure proteins are suitable for protein sequencing and are typically at least 90% pure by weight and preferably at least 95% pure by weight. Given the sequences disclosed herein, as well as the methods provided for identifying substantially homologous mar operons in other species, such substantially pure proteins can be produced and isolated by one of ordinary skill in the art (Maniatis, et al. 1982).

The invention further provides a cloned fusion of a mar regulatory region and a marker locus. In a preferred embodiment, the mar regulatory region is the *E. coli* marO and the marker locus is the β-galactosidase gene, lacZ (see Example 6). Such a fusion on a vector is useful for assaying the ability or inability of compositions to increase or decrease the expression of a Mar phenotype, as disclosed below.

The present invention also provides for the creation of bacterial strains which exhibit the Mar phenotype. In particular, the invention provides such strains by genetic manipulation and provides such strains of *E. coli*.

In one embodiment, anti-sense to the mar repressor locus is introduced within the cells. This may be accomplished by exposing the cells to single-stranded nucleotides or nucleotide analogs which enter the cell. The nucleotides are characterized by substantial anti-sense homology to either the mar repressor locus or its mRNA transcript and are of sufficient length such that they either inhibit the transcription of the mar repressor locus by binding to the mar repressor DNA or they inhibit translation of the mar repressor by binding to the mRNA transcript of the mar repressor locus. More preferably, an operable anti-sense locus is introduced within the cells on a vector. Preferably, the anti-sense locus is operably joined to a strong promoter and on a high copy-number plasmid such that the anti-sense transcripts are expressed at high levels. For some uses, as disclosed below, a temperature sensitive plasmid may be preferred. Given the sequences disclosed herein, as well as the methods provided for identifying substantially homologous mar operons in other species, one of ordinary skill in the art is enabled to produce such nucleotide sequences and vectors operably expressing such sequences.

In a preferred embodiment, a strain is created which has a deletion, insertion or substitution in the chromosomal mar repressor locus such that functional mar repressor is not produced but the mar activator locus is expressed. In a particularly preferred embodiment, a deletion is introduced. This is achieved by cloning the mar operon into a temperature sensitive plasmid which replicates at lower temperatures but does not replicate at higher temperatures. Using appropriate restriction enzymes, any one of numerous possible deletions is introduced into the mar repressor locus on the plasmid. The plasmid is then introduced into bacterial cells and the cells are grown at the lower temperature to allow for homologous recombination to introduce the partially deleted mar repressor locus into the bacterial chromosome. The bacteria are then grown at the higher temperature so that, at cell division, the temperature sensitive plasmid is lost from the daughter cells. Cells in which the deletion was introduced into the chromosome and in which the activator is constitutively expressed may then be selected with antibiotics.

In another preferred embodiment, a mar activator locus is introduced within the cells on a vector. In one embodiment, the mar activator locus is operably joined to the mar regulatory region on a plasmid which does not include an operable mar repressor locus. Homologous recombination is employed, as disclosed above, to inactivate the mar repressor locus on the chromosome by partial deletion, insertion, or substitution, so that functional mar repressor is not produced and the plasmid copy of the mar activator locus is expressed. In a most preferred embodiment, the mar activator locus is operably joined to a regulatory region other than the mar regulatory region such that it is expressed irrespective of the presence of the mar repressor and the chromosomal mar repressor locus need not be inactivated. Preferably, the regulatory region contains a strong promoter. In addition, it is preferred in both embodiments that the plasmids be high copy-number plasmids. For some uses, as disclosed herein, it may be preferable that the plasmid be temperature sensitive. Given the sequences disclosed herein, as well as the methods provided for identifying substantially homologous mar operons in other species, one of ordinary skill in the art is enabled to produce such vectors (see Examples 2 and 3).

The present invention further provides for the creation of bacterial strains which exhibit increased sensitivity to antibiotics, relative to wild-type cells, because they have at least partially lost the ability to express a mar activator. In particular, the invention provides such strains by genetic manipulation and provides such strains of E. coli.

In one embodiment, anti-sense to the chromosomal mar activator locus may be introduced within the cells. This may be accomplished by exposing the cells to single-stranded nucleotides or nucleotide analogs which enter the cell. The nucleotides are characterized by substantial anti-sense homology to either the mar activator locus or its mRNA transcript and are of sufficient length such that they either inhibit the transcription of the chromosomal mar activator locus by binding to the mar activator DNA or they inhibit translation of the mar activator by binding to the mRNA transcript of the mar activator locus. More preferably, an operable anti-sense locus is introduced within the cells on a plasmid. Preferably, the anti-sense locus is operably joined to a strong promoter and on a high copy-number plasmid such that the anti-sense transcripts are expressed at high levels. For some uses, as disclosed below, a temperature sensitive plasmid may be preferred. Given the sequences disclosed herein, as well as the methods provided for identifying substantially homologous mar operons in other species, one of ordinary skill in the art is enabled to produce such nucleotide sequences and vectors operably expressing such sequences.

In another preferred embodiment, a strain is created which has a deletion, insertion or substitution in the chromosomal mar activator locus such that functional mar activator cannot be produced. In another embodiment, a chromosomal deletion, insertion or substitution is introduced which is not in the mar activator locus but which entails a frame-shift upstream of the locus such that functional mar activator protein is not produced. In another preferred embodiment, the entire mar operon or a substantial part of it may be deleted (see Example 7). As disclosed above, such deletions, insertions or substitutions may be achieved by homologous recombination between the chromosomal mar operon and a properly constructed plasmid. To further increase sensitivity to antibiotics, the E. coli ORF 64 and/or ORF 156/157 loci, or their homologs in other species, may be similarly inactivated. Thus, in preferred embodiments, insertions, deletions, substitutions or frame-shifts are introduced into a bacterial chromosome which substantially decrease expression of ORF 64, ORF 156/157 or their homologs.

In a most preferred embodiment, a mar repressor locus is introduced within the cells on a vector. In this embodiment, the mar repressor locus is operably joined to a regulatory region other than a mar regulatory region such that it is expressed irrespective of its own presence. Preferably, the regulatory region will contain a strong promoter and the vectors are high copy-number plasmids. For some uses, as disclosed below, it may be preferable that the plasmid be temperature sensitive. Given the sequences disclosed herein, as well as the methods provided for identifying substantially homologous mar operons in other species, one of ordinary skill in the art is enabled to produce such vectors (see Examples 2 and 3).

The present invention also provides an assay for compositions which induce a Mar phenotype by interfering with the activity of a mar repressor or which increase the sensitivity of cells to antibiotic compositions by enhancing the activity of a mar repressor. In each embodiment, cells which are not characterized by the Mar phenotype are exposed to a composition and then the level of expression of a locus under the control of a mar regulatory region is assayed. The locus may be contained within a mar operon or may be operably joined to a mar regulatory region and introduced into the cells on a vector.

In one embodiment, the level of a protein product of a locus under the control of a mar regulatory region is directly measured. This may be accomplished by, for example, polyacrylamide gel electrophoresis or by any of a variety of other means which are well known to those of ordinary skill in the art.

In another embodiment, the levels of the mRNA transcript of a locus under the control of a mar regulatory region are directly measured. This may be accomplished, as is well known in the art, by performing a Northern hybridization with a probe which has been radioactively labeled with $^{32}p$ and measuring the level of radioactive probe bound. In a preferred embodiment, the locus is a mar operon activator locus (see Example 8). Probes for such a locus are disclosed above. In addition, in another preferred embodiment, the locus is at least one of the open reading frames of the E. coli Region I (see FIG. 1) disclosed in SEQ ID NO: 1.

In a preferred embodiment, a fusion of a marker locus to a mar regulatory region is introduced within the cells. One such fusion is disclosed in Example 6. In one embodiment, the marker fusion of Example 6 is introduced within cells and the cells are then grown in LB broth at 30° C. for one hour in the presence of the compound to be tested. The level of activity of the β-D-galactosidase marker can be determined by the O-nitrophenyl-β-D-galactoside assay described in Maniatis, et al. (1982).

In each of these embodiments, it is further preferred that a vector bearing an operable mar repressor locus be introduced within the cells. This will cause increased repression of the mar operon and improve the ability of the assay to detect inducers of the Mar phenotype. The mar repressor locus is preferably introduced into the chromosome by homologous recombination and is operably joined to a regulatory region other than a mar regulatory region such that it does not repress it own expression. Such vectors are disclosed above.

The most preferred embodiment is an assay employing cells into which have been introduced both a marker locus fused to a mar regulatory region and an operable mar repressor locus which is not controlled by a mar regulatory region.

The present invention also provides assays for compositions which act to prevent the expression of a Mar phenotype or which cause cells to become even more sensitive to certain compounds than wild-type cells, by acting as inhibitors of mar operon expression. In each embodiment, cells which possess an operable mar activator locus are exposed to a composition and then the level of expression of a locus, the expression of which is at least in part controlled by mar operon expression, is assayed. The locus may be naturally occurring in the cells or may be operably joined to a regulatory region influenced by mar operon expression.

As disclosed above, the assay may be a direct assay for a translation product of the locus by, for example, electrophoresis of cellular proteins, for a transcription product of the locus by, for example, a Northern blot of cellular mRNA or, in a preferred embodiment, the locus is a marker locus, the activity of which is easily assayed.

In a most preferred embodiment, a marker locus is operably joined to the regulatory region of an operon which is affected by mar operon expression. Means of identifying such loci are disclosed below. The fusion of the regulatory region and marker is then introduced into cells. After the cells have been exposed to a composition, changes in the level of expression of the marker locus can be assayed as an indication of the effect of the composition on the expression of the mar operon. In a particularly preferred embodiment, the regulatory region is from the micF or ompF loci of *E. coli*. The expression of the micF locus is affected by mar operon expression. The micF locus, in turn, affects the expression of the ompF locus. These loci or their regulatory regions may be operably fused to, for example, lacZ and the activity of the β-D-galactosidase determined as described above. In another preferred embodiment, the regulatory region is marO and the marker locus is one of the loci encoded by the *E. coli* Region I shown in FIG. 1 and disclosed in SEQ ID NO: 1. In this embodiment, the assay is for the transcription or translation products of Region I.

The present invention also provides assays for identifying loci involved in the expression of a Mar phenotype other than mar operons. That is, the invention provides assays for loci whose expression is directly or indirectly regulated by a mar activator protein.

In one embodiment, substantially purified mar activator protein, disclosed above, is mixed with the fragmented genomic DNA of a species under conditions which permit it to bind to appropriate DNA sequences. DNA fragments to which the activator has bound may then be isolated on filters, in polyacrylamide gels, or by other methods well known to those of ordinary skill in the art. Those fragments may then be cloned into vectors and used as probes to locate and isolate their corresponding loci or may be sequenced to identify gene products associated with them.

In another embodiment, a cell line is employed into which has been introduced a vector bearing an operable mar activator locus such that the cells express the Mar phenotype. Preferably, the activator locus is joined to a regulatory region other than the mar regulatory region such that its level of expression is high. Alternatively, the mar repressor locus may be inactivated by deletion, insertion or substitution, as disclosed above and a plasmid bearing an operable activator locus but not an operable repressor locus, as disclosed above, may be introduced within the cells. The total mRNA from these cells may then be compared to the total mRNA of cells which are not expressing the Mar phenotype. In a most preferred embodiment, this is accomplished by creating a cDNA library of the total mRNA from the mar strain and the non-mar strain. This cDNA library is then used to generate probes to screen, by standard Northern technique, the total mRNA from the mar strain and the non-mar strain. Any cDNA probes that hybridize to the mRNA of one strain but not to the mRNA of the other will correspond to loci involved in the expression of the Mar phenotype. Those probes may then be used to identify such loci by standard techniques. An alternative approach would employ subtractive screening. The cDNA from a strain expressing a mar activator locus can be hybridized to excess mRNA from a strain deleted of that locus. Subsequently, those cDNAs which do not hybridize can be isolated by, for example, hydroxyapatite chromatography and used to identify mar related loci.

In another embodiment, a promoterless and therefore inoperable marker locus is introduced into the cell and allowed to insert randomly into the chromosome. The cells are then manipulated so as to change their phenotype either from non-mar to mar or from mar to non-mar. Cells in which the expression of the marker changes along with the change in Mar phenotype, contain markers which have operably inserted into loci which are regulated directly or indirectly by a mar operon (See Example 9). The two alternative versions of this embodiment are described separately, below.

In one version of the above embodiment, the cells do not initially express the Mar phenotype but contain an operable mar operon which is capable of being induced. It is particularly preferred that a vector bearing an operable mar repressor locus, as disclosed above, be introduced within the cells such that the expression of the mar activator locus is initially minimal. A promoterless marker locus contained within a transposon and inserted within a phage, for example λ::TnphoA or λ::TnlacZ, is introduced into the cells and allowed to randomly integrate into the genome. In addition, it is desirable that the transposon also include a locus conferring resistance to kanamycin or another appropriate antibiotic. A number of colonies, preferably at least two thousand and, more preferably, at least ten thousand, are then isolated on plates containing kanamycin or another appropriate antibiotic. These colonies are then examined for expression of the marker locus. If the marker is phoA or lacZ and the cells are grown on plates with 5-bromo-4-chloro-3-indolyl phosphate (XP plates) or 5-bromo-4-chloro-3-indolyl β-D-galactoside (XG plates), colonies in which the marker operably inserted into an actively expressed locus will be blue whereas colonies in which the marker failed to insert, inserted inoperably, or inserted operably into a repressed locus will appear white. The colonies in which the marker is not expressed are then isolated and the cells are grown in the presence of a known inducer of the mar operon (e.g. salicylate or tetracycline for *E. coli*). Subsequent to such treatment, colonies which express the marker (and, in this example, turn blue) are isolated. These colonies contain the marker operably inserted in a locus that is subject to regulation by a mar operon. The DNA of these colonies may then be fragmented and cloned. Those clones which confer resistance to kanamycin or another appropriate antibiotic will contain the marker in the transposon as well as DNA adjacent to the insertion site. The genomic DNA adjacent to the insertion site of the transposon can then be isolated and the locus into which the transposon inserted can be identified by techniques known to those of ordinary skill in the art. That locus will, by this method, be identified as one which is involved in the expression of the Mar phenotype.

In a most preferred version of the above embodiment, the cells initially express the Mar phenotype but can easily be caused to express the non-Mar phenotype. As above, a promoterless marker in a transposon is introduced within the cells and allowed to randomly integrate into the chromosome. And, as above, the transposon also encodes a locus conferring resistance to kanamycin or another appropriate antibiotic. A temperature sensitive plasmid, such as pMAK705 (Hamilton, et al. 1989), bearing an operable mar activator locus is introduced within the cells. The plasmid may bear the activator locus operably joined to a mar regulatory region but without the mar repressor locus or, preferably, may contain an activator locus operably joined to a regulatory region other than a mar regulatory region such that its level of expression is high. If the mar activator locus is operably joined to a mar regulatory region, the chromosomal mar repressor locus must be inactivated by any of the means disclosed above. In addition, the chromosomal mar activator locus is inactivated by any of the means disclosed above so that the expression of the Mar phenotype is dependent upon the plasmid copy of the activator locus and the cells are recombination deficient (e.g. recA__) so that the activator locus on the plasmid cannot be introduced into the chromosome. Initially, the cells are grown at a temperature at which the temperature sensitive plasmid replicates (e.g. 30° C. for pMAK705) and in the presence of kanamycin or another appropriate antibiotic. In this embodiment, a number of colonies, preferably at least two thousand and, more preferably, at least ten thousand, are then isolated and examined for expression of the marker locus. If the marker is phoA or lacZ and the cells are grown on X-P or X-G plates, for example, colonies in which the marker operably inserted into an actively expressed locus will be blue whereas colonies in which the marker failed to insert, inserted inoperably, or inserted operably into a repressed locus will appear white. The colonies in which the marker is expressed are then isolated and the cells are grown at an elevated temperature (e.g. 42° C. for pMAK705) such that the temperature sensitive plasmid and, consequently, the Mar phenotype are lost. Then, colonies which no longer express the marker are isolated. These colonies contain the marker in the transposon operably inserted in a locus that is subject to regulation by a mar operon. As described above, the kanamycin or other resistance locus in the transposon can be used to isolate a fragment containing the transposon and DNA adjacent to the insertion site of the transposon. The locus into which the transposon inserted can then be identified by techniques known to those of ordinary skill in the art. That locus will, by this method, be identified as one which is involved in the expression of the Mar phenotype.

The present invention further provides compositions and a method for their use in treating bacterial infections. By employing the assays disclosed above, one of ordinary skill in the art is enabled to identify compositions which inhibit the expression of a bacterial mar operon. These compositions may be administered to a human or other animal along with known antibiotics. By inhibiting the expression of the mar operon, these compositions will either enhance the effectiveness of the known antibiotic or will render an otherwise ineffective antibiotic effective. Such compositions, once identified by the means disclosed herein, can be combined in pharmaceutically effective amounts with known antibiotics by one ordinarily skilled in the art.

EXAMPLE 1

A mar mutant of *E. coli* K12 designated AG102 was derived from a wild-type strain designated AG100 by selection with antibiotics (see George and Levy, 1983b). AG102 was then subjected to λ b221 c1857 rex::Tn5 mutagenesis. A revertant from the Mar phenotype, resulting from Tn5 insertion within the mar operon, was isolated and designated AG1025. Exploiting the single BamHI site in Tn5, the AG1025 chromosomal DNA was digested with BamHI or partially digested with Sau3A. The resulting fragments were ligated into the single BamHI site of the high copy-number plasmid vector pUC18. Two clones, designated pKanl and pKan2 (see Hachler, Cohen and Levy, 1991), were isolated which contained the 3.2 kbp of Tn5 upstream of its internal BamHI site. A 2 kbp HpaI fragment of pKanl, containing only 187 bp from the IS50L of Tn5 and 1.85 kbp of chromosomal DNA was used as a probe to screen a λ phasmid library derived from partial Sau3A digests of the *E. coli* K12 derivative W3110 (see Elledge and Walker, 1985). Isolation was performed in host strain PLK1738 in which the marA region has been deleted. Two phasmids identified by the probe were introduced by transduction into a deletion strain HH84 in which the region including the mar operon had been deleted from the chromosome. These phasmids were capable of restoring mar operon activity. One of the fragments, 13.1 kbp in length, was used for subcloning into the low copy-number vector pHSG415. mar activity was tested in CH164, a ΔmarA strain genetically related to the original AG100 mar mutants. Subclones containing either the 9 kbp PstI or 7.8 kbp HpaI-PstI fragment, but none containing any smaller fragments, produced Mar mutants. (For detail on the genotypes of the strains and vectors, see Hachler, Cohen, and Levy, 1991, incorporated herein by reference.)

EXAMPLE 2

The mar repressor locus, marR, was cloned from the wild-type plasmid pHHM183 (see Hachler, Cohen and Levy, 1991) as an 818 bp DraI fragment into the SmaI site of the high copy-number cloning vector pUC18. The plasmid was designated p125WT. A mutant mar repressor locus causing expression of the Mar phenotype was cloned on a 850 bp DraI-HpaI fragment from plasmid pKanl (see Hachler, Cohen and Levy, 1991) into pUC18. This plasmid was designated p125mar. These plasmids have been introduced into a number of *E. coli* K12 strains such as the wild-type AG100 and mar mutant AG102. The full genotypes of these strains may be found in Cohen et al., 1988, incorporated herein by reference.

EXAMPLE 3

The entire *E. coli* mar operon, marA, and marB have been cloned into various vectors and introduced within various hosts using the disclosed sequences and the polymerase chain reaction to generate the fragments disclosed below. In particular, for cloning the entire operon, the PCR primers at the 5' end were nucleotides 1311–1328 of SEQ ID NO: 1 and nucleotides 2575–2592 at the 3' end. In addition PstI linkers were included at both ends. For cloning the marA locus, the PCR primers were nucleotides 1893–1908 at the 5' end and nucleotides 2265–2282 at the 3' end with EcoRI linkers at both ends. For cloning the marB locus, the PCR primers were nucleotides 2314–2331 at the 5' end and nucleotides 2515–2532 at the 3' end with EcoRI linkers at both ends. The PCR synthesized genes have been cloned into several plasmid vectors at appropriate single restriction enzyme sites: pUC18, a multicopy ColE1 derivative; pMAK705, a temperature-sensitive plasmid described in Hamilton et al., 1989; and pMAL-C2, a plasmid used for expressing the protein fused to MalE (New England BioLabs, Beverly, Mass., product #800). The plasmids have been introduced in wild-type *E. coli* K12; AG102, a mar mutant described in George and Levy, 1983b; AG1025, a marA::Tn5 mar revertant described in George and Levy 1983b; and CH164, a mar deleted strain described in Hachler, Cohen and Levy, 1991.

EXAMPLE 4

Cloned copies of SEQ ID NO: 1 were digested with BspHI. A resulting 1.24 kbp fragment, corresponding to nucleotides 1073 to 2314 of SEQ ID NO: 1 was used to produce $^{32}$P labelled probes. DNA extracted from a large number of bacterial species were tested for homology to this probe under stringent DNA::DNA hybridization techniques using dot blots and Southern hybridization methods, as are well known to those of ordinary skill in the art (see, e.g., Maniatis, Fritch and Sambrook, 1982, incorporated herein by reference). DNA from the following gram-negative genera were found to hybridize with the probe: Citrobacter, Enterobacter, Escherichia, Hafnia, Klebsiella, Salmonella, and Shigella. Two species, *Enterobacter agglomerans* and *Salmonella sp.*, were further tested. These were found to produce Mar phenotype mutants when selected by the same regime employed with *E. coli* and to produce a 1.4 kb mRNA transcript at heightened levels. The 1.4 kb transcripts were the same size as and homologous to the mRNA produced at heightened levels in *E. coli* expressing the Mar phenotype.

EXAMPLE 5

The *E. coli* marA fragment described in Example 3 was cloned into pMAL-C2, a vector bearing the maltose binding protein locus, MalE. This vector is commercially available as part of a kit for protein purification ("Protein fusion and purification system," New England BioLabs, Beverly, Mass., product #800). The clone, including the marA fragment, encoded a fusion product comprising the mar activator protein and the maltose binding protein linked by a peptide which is cleavable by protease Xa. The fusion protein was made in *E. coli* TB1 (ara, Δ(lac pro AB) rpsL (Φ80 lacZ ΔM15) hsdR). The fusion protein was then substantially purified by amylose column chromatography. The peptide linking the mar activator protein and the maltose binding protein was cleaved and the substantially purified mar protein collected.

EXAMPLE 6

A 405 bp ThaI fragment containing the *E. coli* marO region was ligated into the SmaI site of pMLB1109, a lacZ transcriptional fusion plasmid. The resulting plasmid construct had lacZ gene expression under the control of the marO promoter. The fusion was introduced into the chromosome of a wild type cell and a mar operon deleted strain. This was accomplished by first introducing the marO-lacZ region of the fusion plasmids, by homologous recombination, into the genome of phage λRZ5 by infecting an *E. coli* K12 strain designated SPC103 (M4100 (Δlac U169 araD, rpsL, relA, thi, fibB) deleted of 39 kbp surrounding the mar operon) bearing one of the fusion plasmids, with λRZ5. The resulting lysate was used to transduce plasmid-less SPC103. Amp$^R$, Lac$^+$lysogens were selected on LB agar containing ampicillin (50 μg/ml) and 5-bromo-4-chloro-3-indolyl β-D-galactosidase. Lysates from these purified lysogens were then used to infect *E. coli* MC4100 or SPC103 and Amp$^R$, Lac$_+$lysogens were again isolated. The resulting strains, SPC104, SPC105, SPC106, and SPC107 were confirmed to have a single copy of the fusion region located in the same site on the chromosome (likely the att site) by Southern hybridization of PstI-digested chromosomal DNA from the strains with a 405 bp EcoRI/BamHI fragment. Lysogens of MC4100 (SPC104, SPC105) had 2 bands which hybridized with a 9 kb fragment representing the naturally occurring marO-marA sequence and a larger fragment (>15 kb) representing the insertion of the maro-lacZ fusion phage into the chromosome. The lysogens of the mar deletion strain SPC103 (SPC106, SPC107) contained only chromosomal sequences corresponding to the larger band. DNA manipulations and analyses were performed according to Maniatis et al. (1982). Assays for β-galactosidase activity were performed on cells grown for one hour to mid-logarithmic phase in LB broth in the presence of known and potential inducers of the Mar phenotype at 30° C. The β-galactosidase activity of these cells was compared to cells grown similarly but in the absence of known inducers of the Mar phenotype.

EXAMPLE 7

A 9 kbp PstI fragment of *E. coli* K12 chromosomal DNA containing the mar operon was cloned into temperature-sensitive plasmid pMAK705. The plasmid replicates at 30° C. but is lost from daughter cells during cell division at 42° C. Using BspHI, a 1.24 kbp deletion corresponding to nucleotide 1073 to nucleotide 2314 of SEQ ID NO: 1 and including all of the marO region, the marR and marA loci, and part of the marB locus was made within the mar operon on the plasmid. The plasmid was then introduced within *E. coli* K12 AG100 (see George and Levy, 1983b for genotype information). The plasmid and chromosome were then allowed to undergo homologous recombination and the cells were cured of the plasmid at 42° C. A recombinant strain with the 1.24 kbp deletion in the chromosomal mar operon was isolated and designated AG100 Δ15.

EXAMPLE 8

About 10$^8$ *E. coli* which were not expressing the Mar phenotype were grown at 30° C., collected at the end of logarithmic phase and resuspended in fresh broth containing salicylate, a known mar operon inducer, for one hour at 30° C. The mRNA was extracted from these cells and separated by gel electrophoresis. A 1.24 kb BspHI fragment from within the mar operon which includes the marA locus was labeled with $^{32}$p by random priming and used as a probe in a Northern hybridization to assay for increased expression of the marA locus.

EXAMPLE 9

TnphoA and TnlacZ were used to mutagenize a recA *E. coli* strain which had been deleted of the mar operon and transformed with a temperature-sensitive (curable) plasmid containing the constitutively expressed mar operon. From a total of 2100 fusions, 5 mar-regulated mutants were identified. Two lacZ fusions showed loss of LacZ activity upon loss of the plasmid at 42° C., while three phoA fusions showed an increase in PhoA activity with plasmid loss. The DNA sequence of the chromosomal DNA proximal to each of the fusions did not show homology with any known genes of E. coli. The lacZ fusions were at 31.5 and 14 min; two of the phoA fusions were at 77 min and one was at 51.6 min. In one of the two phoA fusions at 77 min, PhoA activity was associated with the membranes. This approach has identified new genes in E. coli which are regulated by the marRAB operon and involved in the Mar phenotype.

EXAMPLE 10

Based on sequencing of Mar mutants, the protein products of both ORF 125 and ORF 144 were considered candidates for the mar repressor. To investigate this, fusion proteins of the maltose binding protein (MBP) and each of the two potential repressors, MarR125 and MarR144, were produced. MBP-MarR144, but not MBP-MarR125, repressed expression of LacZ from a marO-lacZ fusion. The fusion proteins MBP-MarR125 and MBP-MarR144 were purified by amylose affinity chromatography. Gel retardation studies showed that purified MBP-MarR144 bound to marO with an affinity of $5 \times 10^9 M$. No binding was seen with MBP-MarR125. Therefore the N-terminal amino acid residues lacking in MBP-MarR125 are required for marO binding. Structurally unrelated compounds (tetracycline, chloramphenicol, ampicillin, DNP and salicylate) at different concentrations caused reversal of the binding of MarR (i.e., MBP-MarR144) to marO.

EXAMPLE 11

In conjunction with SEQ ID NO: 1, the polymerase chain reaction (PCR) was employed to amplify the coding sequences of Region I and Region II. PCR primers were created to flank the coding regions of ORF 156/157, ORF 64, Region I, Region II, and Regions I and II together. For cloning ORF 156/157, the PCR primers were nucleotides 570–587 at the 5' end of SEQ ID NO: 1 and nucleotides 1022–1039 at the 3' end with either PstI or EcoRI linkers at the ends. For cloning ORF 64, the PCR primers were nucleotides 1039–1056 at the 5' end and nucleotides 1216–1233 at the 3' end with either PstI or EcoRI linkers at the ends. For cloning the entire Region I sequence, the PCR primers were nucleotides 163–180 at the 5' end and nucleotides 1216–1233 at the 3' end with either PstI or EcoRI linkers at the ends. For cloning Regions I and II together, the PCR primers were nucleotides 163–180 at the 5' end and nucleotides 2575–2592 at the 3' end with PstI linkers at both ends. The PCR synthesized sequences were cloned into several plasmid vectors at appropriate restriction enzyme sites: pMAK705, a temperature-sensitive low copy-number plasmid (Hamilton et al. 1989) and pMAL-C2, a plasmid used for expressing the protein fused to MalE (New England BioLabs, Beverly, Mass.).

Plasmid constructs containing different PCR fragments of Region I and Region II were used in complementation analyses to define the genes required to restore multidrug resistance (to tetracycline, chloramphenicol, nalidixic acid, norfloxacin, and rifampicin) in mar deletion and inactivated strains. In two deletion mutants (Δ39 kb including mar-MCH164; Δ1.2 kb in the mar operon-WY100) plasmids containing marA alone restored wild-type MICs to tetracycline, nalidixic acid, and chloramphenicol. The addition of marB to marA increased the resistance to the drugs 19–46% (depending upon the drug tested), suggesting that both marA and marB are associated with intrinsic drug susceptibility/resistance.

Plasmids containing both Region I and Region II in the same mutant strains further increased antibiotic resistance levels 2–3 fold to levels comparable with Mar mutants. These findings indicate that both Region I and Region II are involved with the multiple antibiotic resistance phenotype. More detailed results are shown below for complementation tests with nalidixic acid (nal), tetracycline (tet) and chloramphenicol (cml).

|  | MIC (µg/ml) | | |
|---|---|---|---|
| E. coli strain | nal | Tet | clm |
| AG100 (wild-type) | 4.2 | 3.3 | 4.6 |
| MCH164 (Δ39kb) | 2.2 | 1.9 | 0.9 |
| MCH164pMAL-marA | 5.3 | 3.4 | 4.9 |
| MCH164pMAL-marB | 2.1 | 2.1 | 1.0 |
| MCH164pMAL-marAB | 6.3 | 4.7 | 7.2 |
| MCH164pMAK-Region II | 6.8 | 4.7 | N/A* |
| MCH164pMAK-Regions I & II | 11.3 | 10.4 | N/A* |
| MCH164pHH193-SEQ ID NO: 1 | 13.6 | 13.1 | N/A* |
| AG102 (Mar mutant) | 14.5 | 13.8 | >25 |

*Plasmid confers resistance to cml.

---

I claim:

1. An isolated nucleic acid molecule comprising a molecule selected from the group consisting of
   (a) a molecule having the sequence of nucleotides 1893–2279 of SEQ ID NO:1,
   (b) a molecule which hybridizes under stringent conditions to a molecule consisting of the sequence of nucleotides 1893–2279 of SEQ ID NO:1, and
   (c) complements of (a) or (b),
   wherein the isolated nucleic acid molecule encodes an activator of a bacterial multiple antibiotic resistance operon.

2. The isolated nucleic acid of claim 1, wherein the isolated nucleic acid comprises SEQ ID NO:1.

3. The isolated nucleic acid molecule of claim 1, wherein the isolated nucleic acid is isolated from a member of the Enterobacteriaceae.

4. The isolated nucleic acid molecule of claim 1, wherein the isolated nucleic acid is free of operable sequences encoding a repressor locus of the bacterial multiple antibiotic resistance operon.

5. The isolated nucleic acid molecule of claim 4 operably linked to a regulatory region.

6. The isolated nucleic acid molecule of claim 5 in a plasmid, and wherein replication of the plasmid is temperature sensitive.

7. The isolated nucleic acid molecule of claim 1 wherein the isolated nucleic acid molecule is labeled.

8. An isolated nucleic acid molecule comprising a nucleic acid molecule having the nucleotide sequence of at least 15 contiguous nucleotides of the nucleic acid of claim 1.

9. The isolated nucleic acid molecule of claim 8, wherein the isolated nucleic acid has the nucleotide sequence of at least 15 contiguous nucleotides of nucleotides 1893–2297 of SEQ ID NO:1.

10. The isolated nucleic acid molecule of claim 8, wherein the isolated nucleic acid is free of operable sequences encoding a repressor locus of the bacterial multiple antibiotic resistance operon.

11. The isolated nucleic acid molecule of claim 10 operably linked to a regulatory region.

12. The isolated nucleic acid molecule of claim 11 in a plasmid, and wherein replication of the plasmid is temperature sensitive.

13. The isolated nucleic acid molecule of claim 8 wherein the isolated nucleic acid molecule is labeled.

14. An isolated antisense nucleic acid which hybridizes under physiological conditions to a MAR operon or transcription product thereof, and which reduces expression of marA.

15. The isolated antisense nucleic acid of claim 14, comprising at least 15 contiguous nucleotides of the isolated nucleic acid of claim 1.

16. The isolated antisense nucleic acid of claim 14, comprising at least 15 contiguous nucleotides of SEQ ID NO:1 or the complement thereof.

17. The isolated antisense nucleic acid of claim 16, wherein the at least 15 contiguous nucleotides are contained within nucleotides 1893–2279 of SEQ ID NO:1.

18. The isolated antisense nucleic acid of claim 14, wherein the isolated antisense nucleic acid is free of operable sequences encoding a repressor locus of the bacterial multiple antibiotic resistance operon.

19. The isolated nucleic acid molecule of claim 17 operably linked to a regulatory region.

20. The isolated nucleic acid molecule of claim 18 in a plasmid, and wherein replication of the plasmid is temperature sensitive.

21. An antibacterial composition comprising an antibiotic composition and a substance which binds to a bacterial multiple antibiotic resistance operon, or a transcription or expression product thereof, and which decreases the expression of marA.

22. The antibacterial composition of claim 21 wherein the substance is an isolated antisense nucleic acid molecule which hybridizes under physiological conditions to the multiple antibiotic resistance operon or a transcription product thereof.

23. The antibacterial composition of claim 22, wherein the antisense nucleic acid molecule comprises at least 15 contiguous nucleotides of SEQ ID NO:1 or the complement thereof.

24. The antibacterial composition of claim 22, wherein the antisense nucleic acid molecule comprises at least 15 contiguous nucleotides of the isolated nucleic acid of claim 1.

25. A bacterial cell into which has been introduced an isolated nucleic acid molecule selected from the group consisting of the isolated nucleic acid molecule of claim 5, the isolated nucleic acid molecule of claim 6, the isolated nucleic acid molecule of claim 11, the isolated nucleic acid molecule of claim 12, the isolated nucleic acid molecule of claim 17 and the isolated nucleic acid molecule of claim 18.

26. The bacterial cell of claim 22, wherein the bacteria are recombination deficient.

27. The bacterial cell of claim 22 or claim 23, wherein the bacteria are free of an operable bacterial multiple antibiotic resistance operon.

* * * * *

UNITED STATES PATENT AND TRADEMARK OFFICE
CERTIFICATE OF CORRECTION

PATENT NO. : 5,817,793
DATED : October 6, 1998
INVENTOR(S) : Stuart B. Levy

It is certified that error appears in the above-identified patent and that said Letters Patent is hereby corrected as shown below:

Column 1,
Line 11, after Related Application and before Field of the Invention, the following should be inserted:

-- Government Funding

This invention was made with goverment support
Under AI16756 awarded by the National Institutes of Health.
The government has certain rights in the invention. --

Signed and Sealed this

Twenty-second Day of April, 2003

JAMES E. ROGAN
*Director of the United States Patent and Trademark Office*